(12) United States Patent
Tong et al.

(10) Patent No.: US 8,858,939 B2
(45) Date of Patent: Oct. 14, 2014

(54) ECTOPIC PREGNANCY TREATMENT

(75) Inventors: Stephen Tong, Canterbury (AU); Ulrika W. Nilsson, Bentleigh (AU); Terence Grant Johns, Box Hill North (AU)

(73) Assignee: Monash University, Clayton, Victoria (AU)

( * ) Notice: Subject to any disclaimer, the term of this patent is extended or adjusted under 35 U.S.C. 154(b) by 564 days.

(21) Appl. No.: 12/896,094

(22) Filed: Oct. 1, 2010

(65) Prior Publication Data
US 2011/0110933 A1 May 12, 2011

Related U.S. Application Data

(60) Provisional application No. 61/248,124, filed on Oct. 2, 2009.

(51) Int. Cl.
| | | |
|---|---|---|
| A61K 45/06 | (2006.01) | |
| A61K 49/14 | (2006.01) | |
| A61K 31/7068 | (2006.01) | |
| A61K 31/708 | (2006.01) | |
| A61K 31/5377 | (2006.01) | |
| A61K 31/7076 | (2006.01) | |
| A61K 31/519 | (2006.01) | |
| A61K 31/517 | (2006.01) | |
| A61K 31/7052 | (2006.01) | |

(52) U.S. Cl.
CPC ......... *A61K 31/5377* (2013.01); *A61K 31/7068* (2013.01); *A61K 31/708* (2013.01); *A61K 31/7076* (2013.01); *A61K 31/519* (2013.01); *A61K 31/517* (2013.01); *A61K 45/06* (2013.01); *A61K 31/7052* (2013.01)
USPC ........ 424/133.1; 514/9.6; 514/43; 514/234.5; 424/9.1; 424/9.34

(58) Field of Classification Search
None
See application file for complete search history.

(56) References Cited

U.S. PATENT DOCUMENTS

| 6,638,543 B2 | 10/2003 | Kang et al. | |
|---|---|---|---|
| 2004/0093624 A1 | 5/2004 | French et al. | |
| 2005/0208095 A1* | 9/2005 | Hunter et al. | 424/423 |
| 2007/0015837 A1* | 1/2007 | Kun et al. | 514/621 |

FOREIGN PATENT DOCUMENTS

WO 98/42364 A1 10/1998

OTHER PUBLICATIONS

Nilsson et al., Clinical Gynecology, Reproductive Sciences, Mar. 2010; 17: 3(Supplement); abstract #327.*
Zambelli et al., Lung Cancer, 2008; 60: 455-457.*
Kim et al., Lung Cancer, 2008; 59: 270-273.*
Phillips, A., J Pharm Pharmacology 53: 1169-1174, 2001.*
Vidal et al.. European Journal of Cancer. 41: 2812-2818, 2005.*
Pirollo et al., Cancer Res. 68(5): 1247-1250, 2008.*
Skubisz et al., BMC Pregnancy and Childbirth, 2013, 13:30, available at biomedcentral.com/1471-2393/13/30; 5 pages total.*
Anteby, et al., "Vascular endothelial growth factor, epidermal growth factor and fibroblast growth factor-4 and -10 stimulate trophoblast plasminogen activator system and metalloproteinase-9," *Molecular Human Reproduction*, vol. 10(4), pp. 229-235 (2004).
Corpa, "Ectopic pregnancy in animals and humans," *Reproduction*, vol. 131, pp. 631-640 (2006).
Darcy, et al., "Selective changes in EGF receptor expression and function during the proliferation, differentiation and apoptosis of mammary epithelial cells," *European Journal of Cell Biology*, vol. 78(7), pp. 511-523 (1999).
Farquhar, "Ectopic pregnancy," *Lancet*, vol. 366, pp. 583-591 (2005).
Feld, et al., "Use of the Epidermal Growth Factor Receptor Inhibitors, Gefitinib (Iressa®) and Erlotinib (Tarceva®), in the Treatment of Non-small Cell Lung Cancer: A Clinical Practice Guideline," *Evidence-Based Series* #7-9: Section 1, 4 pages (2006).
Flint, "Ligand-independent activation of steroid receptors" *Domestic Animal Endocrinology*, vol. 23(1-2), pp. 13-24 (2002).
Hills, et al., "Heparin prevents programmed cell death in human trophoblast," *Molecular Human Reproduction*, vol. 12(4), pp. 237-243 (2006).
Hofmann, et al., "Epidermal Growth Factor and Its Receptor in Human Implantation Trophoblast: Immunohistochemical Evidence for Autocrine/Paracrine Function," *J Clin Endocrinol Metab*, vol. 74, pp. 981-988 (1992).
Humphrey, et al., Epidermal Growth Factor Abrogates Hypoxia-Induced Apoptosis in Cultured Human Trophoblasts through Phosphorylation of BAD Serine 112, "*Endocrinology*,"vol. 149(5), pp. 2131-2137 (2008).
Hung, et al., "Tumor Necrosis Factor-α Converting Enzyme in the Human Placenta Throughout Gestation," *Reproductive Sciences*, vol. 15(2), pp. 195-209 (2008).
Johnson, et al., "The Role of Arachidonic Acid and/or its Metabolites in Embryo Implantation Initiated by Epidermal Growth Factor (EGF)," *Prostaglandins leukotrienes and essential fatty acids*, vol. 52(1), pp. 29-33 (1995).
Johnston, et al., "The anti-inflammatory action of methotrexate is not mediated by lymphocyte apoptosis, but by the suppression of activation and adhesion molecules," *Clin Immunol*, vol. 114, pp. 154-163 (2005).
Johnstone, et al., "Epidermal Growth Factor Stimulation of Trophoblast Differentiation Requires MAPK11/14 (p38 MAP Kinase) Activation," *Biology of Reproduction*, vol. 73(6), pp. 1282-1288 (2005).
Johnstone, et al., "Multiple Anti-apoptotic Pathways Stimulated by EGF in Cytotrophoblasts," *Placenta*, vol. 26, pp. 548-555 (2005).

(Continued)

*Primary Examiner* — Christina Borgeest
(74) *Attorney, Agent, or Firm* — Kilpatrick Townsend & Stockton LLP

(57) ABSTRACT

The invention pertains to methods for treating ectopic pregnancy. More particularly, the present invention relates to methods for treating unruptured ectopic pregnancy using a non-surgical method comprising the administration of an EGFR inhibitor alone or in combination with an anti-metabolite e.g. methotrexate (MTX). The methodology is potentially applicable to treatment of unruptured ectopic pregnancies of all sizes.

14 Claims, 24 Drawing Sheets

(56) References Cited

OTHER PUBLICATIONS

Joyner, et al., "Desmoid Cell Motility Is Induced In Vitro by rhEGF," *Journal of Orthopaedic Research*, vol. 27(9), pp. 1258-1262 (2009).

Kawano, et al., "The effect of epidermal growth factor on vascular endothelial growth factor secretion by endometrial stromal cells," *Clinical and experimental medicine*, vol. 2(2), pp. 69-75 (2002).

Kelly, et al., "Delivery of a Healthy Baby After First-Trimester Maternal Exposure to Lapatinib," *Clinical Breast Cancer*, vol. 7(4), pp. 339-341 (2006).

Lamarca, et al., "Epidermal growth factor-stimulated extravillous cytotrophoblast motility is mediated by the activation of PI3-K, Akt and both p38 and p42/44 mitogen-activated protein kinases," *Human Reproduction*, vol. 23(8), pp. 1733-1741 (2008)

Lockwood, et al., Regulation of plasminogen activator inhibitor 1 expression by interaction of epidermal growth factor with progestin during decidualization of human endometrial stromal cells, *American Journal of Obstetrics and Gynecology*, vol. 184(5), pp. 798-804 (2001).

Merisio, et al., "Single-dose methotrexate for ectopic pregnancy treatment preliminary data," *Acta Bio Med*, vol. 76, pp. 33-36 (2005).

Mok, et al., "Gefitinib or Carboplatin-Paclitaxel in Pulmonary Adenocarcinoma," *N Engl J Med*, vol. 361, pp. 947-957 (2009).

Mol, et al., "Current evidence on surgery, systemic methotrexate and expectant management in the treatment of tubal ectopic pregnancy: a systematic review and meta-analysis," *Human Reproduction*, vol. 14(4), pp. 309-319 (2008).

Nilson, et al., "Methotrexate and Epidermal Growth Factor Inhibition regress placental-derived tissues in vitro and in vivo: towards a novel combination medical therapy to treat ectopic pregnancy," Poster abstract, (published Oct. 6, 2009).

Noonberg, et al., "Tyrosine Kinase Inhibitors Targeted to the Epidermal Growth Factor Receptor Subfamily" *Drugs*, vol. 59(4), pp. 753-767 (2000).

Ribeiro, et al., "Epidermal growth factor modulation of prostaglandins and nitrite biosynthesis in rat fetal membranes," *Prostaglandins leukotrienes and essential fatty acids*, vol. 70(1), pp. 33-40 (2004).

Rosell, et al., "Screening for Epidermal Growth Factor Receptor Mutations in Lung Cancer," *N Engl J Med*, vol. 361, pp. 958-967 (2009).

Skubisz, et al., "The Evolution of Methotrexate as a Treatment for Ectopic Pregnancy and Gestational Trophoblastic Neoplasia: A Review," *ISRN Obstet Gynecol*, 8 pages (2012).

Stovall, et al., "Serum progesterone and uterine curettage in differential diagnosis of ectopic pregnancy," *Fertil Steril*, vol. 57, pp. 456-458 (1992).

Zheng, et al., "Activation of the Mitogen-Activated Protein Kinase Cascade Is Necessary But Not Sufficient for Basic Fibroblast Growth Factor- and Epidermal Growth Factor-Stimulated Expression of Endothelial Nitric Oxide Synthase in Ovine Fetoplacental Artery Endothelial Cells," *Endocrinology*, vol. 140(3), pp. 1399-1407 (1999).

* cited by examiner

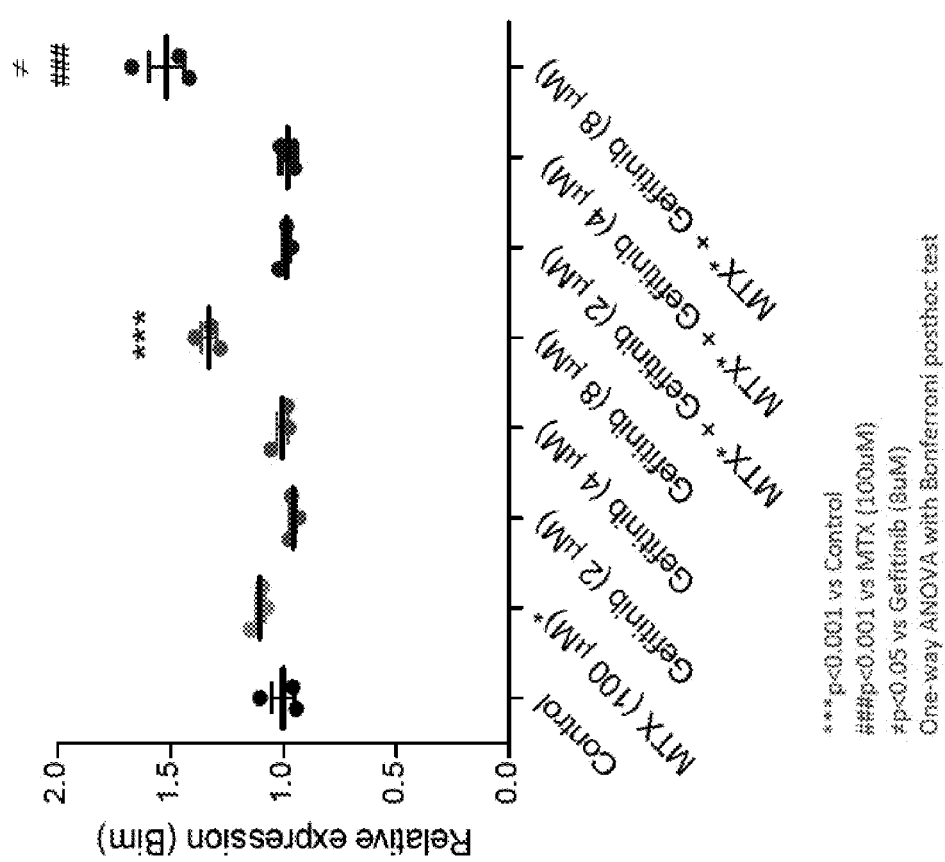

ECTOPIC PREGNANCY TREATMENT

CROSS-REFERENCE TO RELATED APPLICATIONS

The present application claims priority from U.S. 61/248,124, filed Oct. 2, 2009 the content of which is incorporated herein by reference.

FIELD OF THE INVENTION

The invention pertains to methods for treating ectopic pregnancy. More particularly, the present invention relates to methods for treating unruptured ectopic pregnancy using a non-surgical method comprising the administration of an EGFR inhibitor alone or in combination with an anti-metabolite e.g. methotrexate (MTX). The methodology is potentially applicable to treatment of unruptured ectopic pregnancies of all sizes.

BACKGROUND OF THE INVENTION

(i) Ectopic Pregnancy

Ectopic pregnancy denotes a pregnancy occurring elsewhere than in the cavity of the uterus. In humans, it accounts for approximately 1-2% of all pregnancies (approximately 100,000/yr in USA and 10,000/yr in UK). This pathology has been recognised for years and it causes numerous maternal deaths during the first trimester of pregnancy. The causes and mechanisms leading to an ectopic implantation of the ovum are not always clearly defined. Two types of ectopic pregnancy are mainly recognised: (i) tubal pregnancy occurs when an oocyte is fertilized and then remains in the fallopian tube and (ii) other types of pregnancy including abdominal, cervical and ovarian ectopics. These latter types represent approximately 1% of all ectopic pregnancies. While both types of ectopic pregnancies are found in human and animal species, tubal ectopic pregnancies would appear to be restricted to primates.

(ii) Diagnosis and Treatment of Ectopic Pregnancy

It has been reported that in humans an oviductal localisation of the embryo accounts for approximately 95-98% of all ectopic pregnancies and that approximately 1% of oviductal pregnancies are bilateral. Ectopic pregnancies residing in the distal two thirds of the tube are the most frequent, accounting for 85% to 95% of all tubal ectopic pregnancies. In humans, the primary cause of tubal implantation is thought to be an impairment of tubal transport, often as a result of scarring from chronic inflammatory disease or previous tubal surgery. Oviductal pregnancies are often misdiagnosed for abortion, pelvic inflammatory disease, ovarian cysts and uterine leiomyomas. Unequivocal histological documentation of ectopic pregnancy requires the presence of chorionic villi or fetal tissue within the oviduct.

A diagnosis of ectopic pregnancy is usually made by quantitative measurement of the β subunit of human chorionic gonadotropin (β-hCG) and transvaginal ultrasound. The combined approach detects ectopic pregnancy with 97% sensitivity and 95% specificity, avoiding the need for further tests such as dilatation and curettage. This has improved the accuracy of diagnosis and facilitated the earlier detection of ectopic pregnancies than was previously possible.

Timely diagnosis of ectopic pregnancy allows the clinician to consider the full range of treatment options. Therapeutic options for women with tubal ectopic pregnancy are surgery, medical treatment or expectant management. Approximately 90-95% of ectopics are stable without rupture when diagnosed. Of the remaining 5-10% where the ectopic has either ruptured, or there is clinical suspicion of rupture on clinical assessment, then surgery is the only treatment option. In surgery, laparoscopy is now the accepted approach to perform either salpingostomy (incision into the fallopian tube to remove the ectopic) or salpingectomy (removal of the ectopic and the whole fallopian tube). If there are concerns of rapid bleeding from a ruptured ectopic, then the surgical approach is laparotomy and salpingectomy.

(iii) Methotrexate Treatment in Ectopic Pregnancy

Treatment with methotrexate is an alternative to surgery in women who present with unruptured ectopic pregnancy. Methotrexate is a folinic acid antagonist that blocks DNA, and to some extent RNA, synthesis and cell division. As a result, tissues with a rapid turnover such as trophoblasts (i.e. placental tissue), are particularly sensitive to such agents. This is highlighted by the fact that single agent methotrexate (in high doses) is an effective therapy to treat hydatidiform molar pregnancies. These are locally invasive tumours of placental origin.

Treatment with methotrexate is amenable to only a minority of stable ectopic pregnancies, typically about 25% that meet strict clinical criteria. These clinical criteria include a gestational sac size of less than 3 cm, no beating fetal heart, no bleeding into the abdomen, no rupture of the fallopian tube and a maternal serum β-hCG concentration of less than 3000 IU/L (from a venous blood sample). Provided the criteria are met, then an intramuscular course of methotrexate is administered in lieu of surgery. If a decline in the concentration of methotrexate of ≥15% is observed between day 4 to day 7, where day 1 is the first day of methotrexate administration, then the treatment is deemed to be working. However, methotrexate treatment is associated with certain side effects. Serious adverse events include severe neutropenia and alopecia, however these are typically associated with long-term administration of methotrexate. Less serious side effects include nausea, vomiting, diarrhoea, gastritis, abnormal liver function tests, stomatitis and bone marrow suppression. These events limit the dose of methotrexate that can be used to treat ectopic pregnancy. Furthermore, the efficacy of methotrexate falls with increasing ectopic size. Accordingly, these issues substantially impact on its efficacy in successfully resolving ectopic pregnancies.

Given the low frequency of ectopic pregnancies that are amenable to non-surgical intervention, there remains a need for non-surgical treatment options that target a broader number of stable ectopic pregnancies. Furthermore, since around 90% of ectopic pregnancies present without clinical evidence of rupture, potentially most of these stable ectopic pregnancies could be treated medically instead of surgically if an efficacious therapeutic existed.

SUMMARY OF THE INVENTION

The present inventors have developed methods for the treatment of stable (i.e. unruptured) ectopic pregnancy. The methods provide an alternative to the use of surgery as a means for removing the ectopic pregnancy.

The pathological condition of ectopic pregnancy does not frequently occur in laboratory animals and typically the cases are only anecdotal. Owing to the fact that human placentation is a particularly erosive process compared to other species, ectopic pregnancies appear largely to be restricted to humans and rarely non-human primates. Consequently, there does not exist a readily available laboratory animal model in which to study the condition.

In work leading up to the present invention, the inventors developed both in vitro and artificial in vivo models to test the efficacy of the EGFR inhibitor gefitinib alone or in combination with methotrexate in regressing placenta-derived tissue.

These studies demonstrated that blocking EGFR signalling may have a significant negative impact on placental tissues, alone or in combination with methotrexate. The use of EGFR inhibitors has not previously been investigated in the ectopic pregnancy setting and their use is only approved for cancer therapeutics. The inventors have shown that EGFR inhibitors induce significant regression of placental-derived tissue both in vitro and in vivo.

Surprisingly, the inventors also found that the combination of methotrexate and EGFR inhibitor was supra additive in causing regression of placental tissue both in vitro and in vivo. These finding have significant implications for the treatment of ectopic pregnancy. Because only a small percentage of ectopic pregnancies are amenable to treatment using non-surgical methods, the present invention provides a means to treat unruptured ectopic pregnancies of potentially any size. Furthermore, it will be appreciated that due to the synergistic effect of the EGFR inhibitor and methotrexate, lower doses of methotrexate can potentially be used thus minimising adverse side effects which are typically associated with methotrexate treatment.

Accordingly, in one embodiment, the present invention provides a method of treating ectopic pregnancy in a subject comprising administering to the subject a composition comprising an epidermal growth factor receptor (EGFR) inhibitor and optionally an anti-metabolite.

In another embodiment, the invention provides a method of treating ectopic pregnancy in a subject comprising administering to the subject a composition comprising an epidermal growth factor receptor (EGFR) inhibitor in combination with an anti-metabolite.

In another embodiment, the invention provides a method of treating ectopic pregnancy in a subject comprising administering to the subject a composition comprising gefitinib in combination with methotrexate.

In another embodiment, the invention provides for the use of a composition comprising an EGFR inhibitor and optionally an anti-metabolite for treating ectopic pregnancy in a subject.

In another embodiment, the invention provides for the use of a composition comprising an EGFR inhibitor in combination with an anti-metabolite for treating ectopic pregnancy in a subject.

In another embodiment, the invention provides for the use of a composition comprising an EGFR inhibitor and optionally an anti-metabolite in the manufacture of a medicament for treating ectopic pregnancy in a subject.

In another embodiment, the invention provides for the use of a composition comprising an EGFR inhibitor in combination with an anti-metabolite in the manufacture of a medicament for treating ectopic pregnancy in a subject.

In another embodiment, the invention provides for the use of a composition comprising gefitinib in combination with methotrexate in the manufacture of a medicament for treating ectopic pregnancy in a subject.

The anti-metabolite according to the invention may be selected from the group consisting of folic acid antagonist, pyrimidine antagonist, purine antagonist and adenosine deaminase inhibitor.

Preferably, the antimetabolite is selected from the group consisting of methotrexate, 5-fluorouracil, foxuridine, cytarabine, capecitabine, gemcitabine, 6-mercaptopurine, 6-thioguanine, cladribine, fludarabine, nelarabine and pentostatin.

More preferably, the antimetabolite is methotrexate.

In one embodiment, methotrexate is administered orally to the subject in a dose range of from about 2.5 mg to about 50 mg per week, of from about 3 mg to 40 mg per week, of from about 4 mg to 30 mg per week, of from about 5 mg to 20 mg per week.

The methotrexate may be administered as a single or divided dose over the period of one week. For example, preferably the methotrexate is administered on days 1, 4 and 7 in a dosing week.

In another embodiment, methotrexate is administered parentally to the subject at a dose of about 50 mg per $m^2$ body-surface area, or about 1 mg/kg once weekly.

The EGFR inhibitor according to the invention can be any inhibitor that specifically suppresses EGFR function, including antisense and RNAi nucleotide inhibitors, peptide nucleic acids, peptide antagonists, monoclonal antibodies and small molecule inhibitors. In particular, the EGFR inhibitor is a small molecule that specifically suppresses the kinase function of EGFR, or a monoclonal antibody or other compound that competes with EGF for ligand binding to the receptor. Examples of suitable small molecule and antibody EGFR inhibitors that are suitable for use in the present invention include, but are not limited to those provided in Table 1.

TABLE 1

| Drug | Type | Company |
| --- | --- | --- |
| gefitinib | SMI | AstraZenica |
| Erlotinib/Tarceva | SMI | OSI-pharmaceuticals |
| cetuximab | Ab | Merck Serono |
| Lapatinib/Tykerb | Ab | GlaxoSmithKline |
| Panitumumab/Vectibix | Ab | Amgen |
| TheraCIM h-R3/Nimotuzumab | Ab | YM Biosciences |
| matuzumab | Ab | Merck |
| MDX447 | Ab | Medarex/Merck |
| PKI166 | SMI | Novartis |
| Cl-1033 | SMI | Pfizer |
| EKB-569 | SMI | Wyeth |
| GW2016 | SMI | GlaxoSmitheKline |
| zalutumumab | Ab | Genmab |
| Pertuzumab/Omnitarg | Ab | Genentech |

In one embodiment, the EGFR inhibitor is gefitinib.

In one embodiment, the EGFR inhibitor is gefinitib which is administered to the subject orally at a dose of about 250 mg once daily.

It will be appreciated the persons skilled in the art of the invention will be able to determine the appropriate dosing and scheduling of the EGFR inhibitor and anti-metabolite. For example, the relevant doses can be titrated in a subject to find optimal doses that result in a reduction in β-hCG concentration in a subject's bodily fluid and/or reduction in the size of the ectopic pregnancy. Furthermore, where it is desired to use an agent which has already been approved by a regulatory authority, albeit for another indication, the approved dose may provide a useful starting point.

In another embodiment, the anti EGFR antibody according to the invention is selected from the group consisting of a monoclonal antibody, a chimeric antibody, a humanized antibody and a recombinant antibody.

The anti-metabolite and EGFR inhibitor may be administered concurrently or sequentially.

In another embodiment, the invention provides a method of treating ectopic pregnancy in a subject comprising the steps of:
(i) diagnosing an ectopic pregnancy in a subject;
(ii) administering to the subject an EGFR inhibitor optionally in combination with anti-metabolite;
(iii) measuring the concentration of β-hCG in the subject's bodily fluid;
wherein a reduction in the concentration of β-hCG is indicative of successful treatment of the ectopic pregnancy.

In one example, a reduction in the concentration of β-hCG is at least 15% between day 4 and day 7 (where day 1 is the first date of anti-metabolite dose).

In another example, a reduction in the concentration of β-hCG is a reduction in β-hCG levels in a subject's bodily fluid to pre-pregnancy levels (<5 IU/L).

Given the supra-additive effects of the combined treatment of the anti-metabolite methotrexate and EGFR inhibitor gefitinib observed in the ectopic pregnancy models of the present invention, it follows that one of the advantages of the present invention is the ability of the EGFR inhibitor to enhance the efficacy of the standard methotrexate protocol. Therefore, the methods of the invention extend to the treatment of ectopic pregnancies which fall outside the usual clinical criteria by which surgical intervention is necessary.

Accordingly, in another embodiment, the present invention provides a method of treating an ectopic pregnancy having one or more of the following characteristics selected from the group consisting of:
(i) a gestational sac size in the range of from about 0.5 cm to about 10 cm; and
(ii) a β-hCG concentration in the range of from about 200 to about 100,000 IU/L;
wherein the method comprises administering to the subject a composition comprising an EGFR inhibitor in combination with an anti-metabolite.

In one example, the gestational sac size is in the range of from about 1 cm to about 8 cm. In another example, the gestational sac size is in the range of from about 3 cm to about 6 cm. In another example, the gestational sac size is in the range of from about 3 cm to about 5 cm.

In another embodiment, the invention provides a method of treating an unruptured ectopic pregnancy of any size in a subject comprising administering to the subject an EGFR inhibitor optionally in combination with an anti-metabolite.

In another embodiment, the invention provides a method of treating an unruptured ectopic pregnancy of any size in a subject comprising administering to the subject an EGFR inhibitor in combination with anti-metabolite.

The anti-metabolite and EGFR inhibitor agents according to the invention may be administered to the subject according to any of the currently accepted modes of administration of pharmaceutical compositions, including, but not limited to intradermal, intramuscular, intraperitoneal, intravenous, subcutaneous, intranasal, epidural and oral routes.

In one example, the anti-metabolite is administered intramuscularly to the subject. In another example, the EGFR inhibitor and anti-metabolite are administered intravenously, intramuscularly, intraperitoneally or subcutaneously to the subject. In another example, the antimetabolite is administered intramuscularly and the EGFR inhibitor is administered orally to the subject.

In one further example, methotrexate is administered intramuscularly and gefitinib is administered orally to the subject.

In another example, the EGFR inhibitor and anti-metabolite are administered orally to the subject. In a further example, both methotrexate and gefitinib are administered orally to the subject.

In one embodiment, the invention provides a pharmaceutical composition comprising an EGFR inhibitor and optionally an anti-metabolite for the treatment of ectopic pregnancy in a subject.

In another embodiment, the invention provides a pharmaceutical composition comprising an EGFR inhibitor in combination with anti-metabolite for the treatment of ectopic pregnancy in a subject.

In another embodiment, the invention provides a pharmaceutical composition comprising an EGFR inhibitor and optionally an anti-metabolite when used in the treatment of ectopic pregnancy in a subject.

In another embodiment, the invention provides a pharmaceutical composition comprising EGFR inhibitor in combination with an anti-metabolite when used in the treatment of ectopic pregnancy in a subject.

Preferably, the pharmaceutical compositions of the invention comprise a pharmaceutically acceptable carrier.

If the EGFR inhibitor or anti-metabolite is one which is already approved for human use by a regulatory authority, then typically the pharmaceutically acceptable carrier will be that present in the approved formulation.

In another embodiment, the invention provides a method for predicting whether a subject's ectopic pregnancy will be successfully treated comprising:
(i) administering to the subject one or more doses of an EGFR inhibitor optionally in combination with an anti-metabolite; and
(ii) measuring the concentration of β-hCG in the subject's bodily fluid;
wherein a reduction in the concentration of β-hCG by at least 15% between day 4 and day 7 (where day 1 is the first day of anti-metabolite dose) is predictive of successful treatment of the ectopic pregnancy.

In another embodiment, a reduction in the size of the ectopic pregnancy between doses of anti-metabolite is predictive of successful treatment of the ectopic pregnancy.

The subject according to the invention is preferably a female mammal. More preferably, the subject according to the invention is a female primate. Still more preferably, the subject according to the invention is a female human.

DETAILED DESCRIPTION OF THE INVENTION

Figure 1:
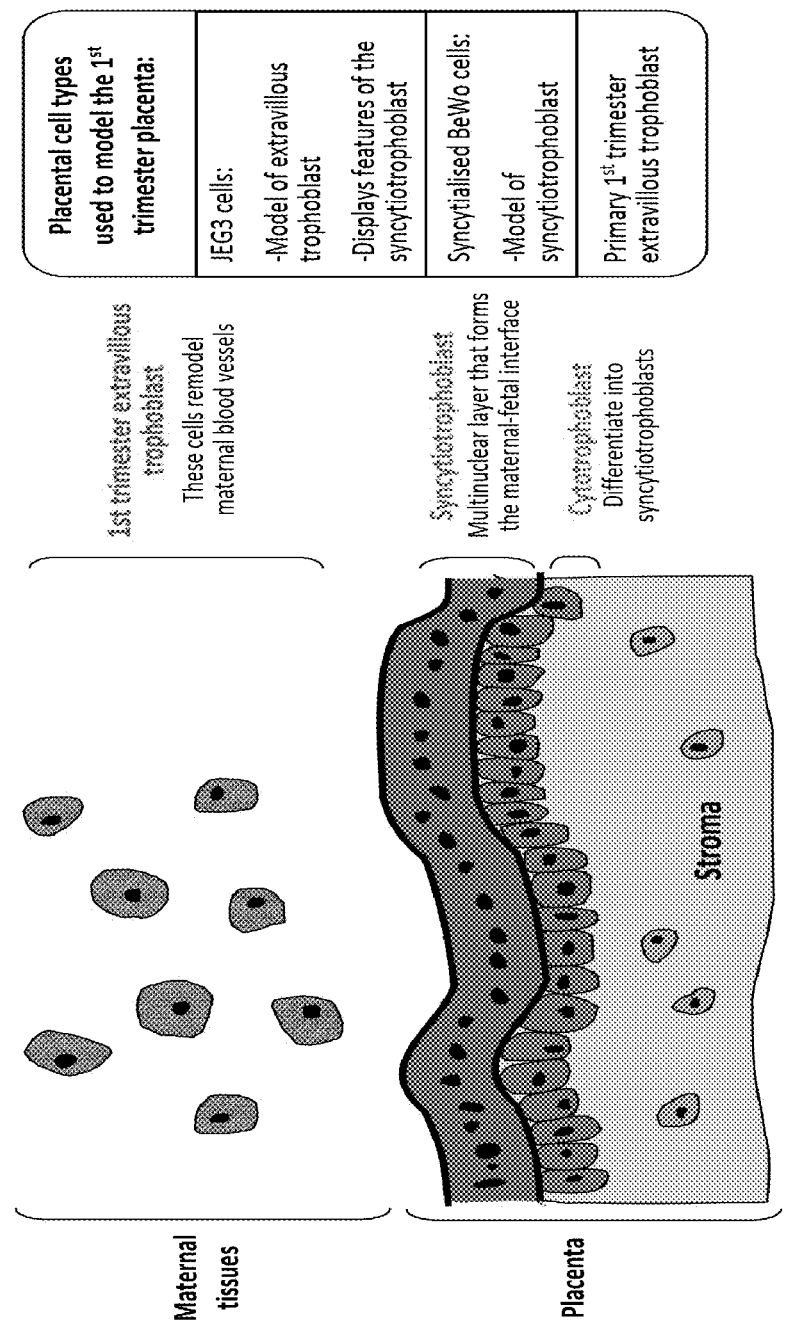
FIG. 1 shows a description of the first trimester placenta and placental cell types used in the examples.

By "ectopic pregnancy" it is meant an extrauterine pregnancy that occurs elsewhere than within the uterine cavity. The term "ectopic pregnancy" is most frequently used to refer to a fallopian tubal pregnancy. The term also encompasses abdominal, cervical and ovarian ectopics. The term as used in the present invention is intended to refer to an unruptured ectopic pregnancy.

The term "EGFR inhibitor" as used according to the invention includes EGFR inhibitors described below or EGFR signalling inhibitors or inhibitors of kinases downstream of EGFR kinases.

The term "in combination with" as used herein is intended to mean that the anti-metabolite and EGFR inhibitor can be administered sequentially or concurrently. Sequential doses may be administered on the same day or on different days. The invention is also intended to include combinations comprising at least one EGFR inhibitor in combination with at least one anti-metabolite. Thus the invention includes combinations comprising different types of EGFR inhibitor together with an anti-metabolite or different types of anti-metabolite agents in combination with an EGFR inhibitor or combinations comprising more than one type of anti-metabolite in combination with more than one type of EGFR inhibitor.

The term "antibody," as used herein, refers to immunoglobulin molecules and immunologically active portions or fragments of immunoglobulin molecules, including T cell receptor molecules, i.e., molecules that contain an antigen binding site that immunospecifically binds an antigen. As such the term "antibody" encompasses not only whole antibody molecules, but also antibody multimers and antibody fragments and/or variants (including derivatives) of antibodies, antibody multimers and antibody fragments. Examples of molecules which are described by the term "antibody" herein include, but are not limited to: single chain Fvs (sdFvs), Fab fragments, Fab' fragments, F(ab')$_2$, disulfide linked Fvs (sd-Fvs), Fvs, and fragments comprising or alternatively consisting of, either a $V_L$ or a $V_H$ domain. The term "single chain Fv" or "scFv" as used herein refers to a polypeptide comprising a $V_L$ domain of antibody linked to a $V_H$ domain of an antibody.

Antibodies of the invention include, but are not limited to, recombinant, monoclonal, multispecific, human, humanized or chimeric antibodies, veneered antibodies, single chain antibodies, Fab fragments, F(ab') fragments, fragments produced by a Fab expression library, anti-idiotypic (anti-Id) antibodies (including, e.g., anti-Id antibodies to antibodies against a receptor molecule of the antigen of the present invention), intracellularly-made antibodies (i.e., intrabodies), and epitope-binding fragments of any of the above.

The compositions according to the invention will be understood to contain therapeutically effective amounts of the anti-metabolite and the EGFR inhibitor. By "therapeutically effective amount" it is meant an amount required to achieve a desired end result weighted against any toxic or detrimental side effects to the subject. The amount required to achieve the desired end result will depend on the nature of the specific EGFR inhibitor used (whether or not in combination with methotrexate), which can be determined without undue experimentation, and the conditions, or disorders being treated, and can be determined by standard clinical techniques. In addition, in vitro assays may optionally be employed to help identify optimal dosage ranges. The precise dose to be employed will also depend on the route of administration and the seriousness of the disease or disorder, and should be decided according to the judgment of the practitioner and each subject's circumstances. Effective doses may be extrapolated from dose-response curves derived from in vitro or animal model test systems.

In the present context, a "therapeutically effective amount" will be understood to mean to amount sufficient to cause a reduction in the β-hCG concentration in a bodily fluid of the subject and/or size of the ectopic pregnancy. A therapeutically effective amount will preferably be a dose which results in a reduction in the β-hCG concentration in a bodily fluid of a subject of at least 15% between successive measurements (typically between day 4 and day 7, where day 1 is the first day of the anti-metabolite dose). A therapeutically effective amount can also refer to a dose or doses of anti-metabolite or EGFR inhibitor that cause the β-hCG concentration in a bodily fluid of the subject to fall below 200 IU/L, preferably down to a non-pregnancy level of about <5 IU/L. A therapeutically effective amount will also be understood to mean a dose or doses of anti-metabolite or EGFR inhibitor that result in the reduction in size of the ectopic pregnancy.

As used herein the terms "treating", "treat" or "treatment" include administering a therapeutically effective amount of the composition according to the sufficient to cause a reduction in one or more of the following (i) trophoblast cell viability, (ii) size of the fertilised ovum and (iii) reduction in the concentration of β-hCG.

The treatment of ectopic pregnancy includes, but is not limited to, alleviating symptoms associated with ectopic pregnancy such as persistent abdominal pain, vaginal bleeding, sweating, fainting, diarrhoea or melena/hematochezia.

Epidermal Growth Factor Receptor

The epidermal growth factor receptor (EGFR, ErbB-1, HER1) is the cell-surface receptor for members of the epidermal growth factor family of extracellular protein ligands. The epidermal growth factor receptor is a member of the ErbB family of receptors, a subfamily of four closely related receptor tyrosine kinases EGFR (ErbB-1), HER2/c-neu (ErbB-2), Her 3 (ErbB-3) and Her 4 (ErbB-4).

EGFR is a transmembrane protein that includes a bound protein tyrosine kinase (PTK) in the intracellular or cytoplasmic portion. After EGF or growth factor alpha (TGFα) binds to the extracellular portion of the EGFR, the intracellular portion having PTK moiety can be activated by phosphorylation with ATP releasing ADP in the process.

Upon activation by its growth factor ligands, EGFR undergoes a transition from an inactive monomeric form to an active homodimer. In addition, to forming homodimers after ligand binding, EGFR may pair with another member of the ErbB receptor family to create an activated heterodimer. EGFR dimerization stimulates its intrinsic intracellular protein-tyrosine kinase activity. As a result, autophosphorylation of several tyrosine resides in the C-terminal domain of EGFR occurs. This autophosphorylation elicits downstream activation and signalling by several other proteins that associate with the phosphorylated tyrosines through their SH2 domains. These downstream signalling proteins initiate several signal transduction cascades, principally the MAPK, Akt and JNK pathways leading to DNA synthesis and cell proliferation (Oda K et al., (2005) *Mol. Syst. Biol.* 1:2005.0010 Epub 2005 May 25). Such proteins modulate phenotypes such as cell migration, adhesion and proliferation.

EGFR signalling also activates a potent cell survival response (Herbst R S et al., (2004) *Nat Rev Cancer* 4:956).

Overexpression of EGFR has been associated with a number of cancers, including lung cancer and gliobastoma. Mutations, amplifications or misregulations of the EGFR or family members are implicated in approximately 30% of all epithelial cancers.

Given its implication in cancer, therapeutics directed against EGFR have been developed which have focussed on cancer treatment.

Epidermal Growth Factor Receptor Inhibitors

It has been previously reported that both epidermal growth factor (EGF) and the EGFR play key roles in placental development and function and the EGFR is expressed in human placenta (Hofmann G E et al., (1992) *J Clin Endocrinol Metab* 74:981). It has been found that EGF not only regulates development and function of normal placenta but also plays a key role in protecting the trophoblasts from the death inducing effects of multiple exogenous stimuli (Humphrey R G et al., (2008) *Endocrinology* 149(5):2131). Nevertheless, treatment of ectopic pregnancy using EGFR inhibitors has not previously been investigated since the focus of EGFR inhibitors has concentrated on cancer therapeutics.

Recently, a study has reported the use of lapatinib in a pregnant woman (Kelly H et al (2006) *Clinical Breast Cancer* 7(4):339). It was found that administration of lapatinib for 11 weeks to a woman who conceived while being treated on a clinical trial resulted in no ill effects on the developing embryo and the delivery of a healthy baby. Accordingly, this study would suggest that EGFR inhibitors such as lapatinib would be unsuitable as agents for the treatment of ectopic pregnancy due to lack of effect on the developing fetus.

Nevertheless, in contrast to the above study, the present inventors have found that EGFR inhibitors induce significant regression of placental-derived tissue both in vivo and in vitro and have been proposed as a treatment for ectopic pregnancy.

The EGFR inhibitors according to the invention include small molecules, an antibody directed against EGFR, immunotoxin conjugates, ligand binding cytotoxic agents and oligonucleotide or peptide aptamers. Various approaches for inhibiting the kinase activity of EGFRs is described in for example, Noonberg S B et al., (2000) *Drugs* 59(4) 753.

A nucleic acid aptamer (adaptable oligomer) is a nucleic acid molecule that is capable of forming a secondary and/or tertiary structure that provides the ability to bind to a molecular target. An aptamer library is produced, for example, by cloning random oligonucleotides into a vector (or an expression vector in the case of an RNA aptamer), wherein the random sequence is flanked by known sequences that provide the site of binding for PCR primers. An aptamer with increased activity is selected, for example, using SELEX (Systematic Evolution of Ligands by EXponential enrichment). Suitable methods for producing and/or screening an aptamer library are described, for example, in Elloington and Szostak, Nature 346:818-22, 1990.

Small molecules inhibitors have been developed for inhibiting EGFR, as well as for such kinases as JNK, MEKK and others that activate EGFR signalling. Exemplary US patents include U.S. Pat. Nos. 5,914,269 and 6,187,585 for EGFR inhibition, U.S. Pat. Nos. 5,877,309, 6,133,246 and 6,221,850 for JNK inhibition, U.S. Pat. No. 6,168,950 for MEKK inhibition and others such as U.S. Pat. Nos. 6,054,440, 6,159,697 and 6,262,241.

Gefinitinib (Iressa®)

Gefinitinib (N-(3-chloro-4-fluorophenyl)-7-methoxy-6-(3-morpholinopropoxy)quinazolin-4-amine) is a small molecule tyrosine kinase selective inhibitor of the EGFR. The compound is indicated for the third line treatment of patients with locally advanced or metastatic non-small cell lung cancer (NSCLC) who have previously failed chemotherapy. It is typically administered in tablet form and the recommended dosage is one 250 mg tablet once a day. There is no data on the use of gefitinib in pregnant women.

Erlotinib (Tarceva®)

Erlotinib (N-(3-ethynylphenyl)-6,7-bis(2-methoxyethoxy)quinazolin-4-amine) is a tyrosine kinase inhibitor indicated for the second or third line treatment of locally advanced or metastatic non-small cell lung cancer (NSCLC) after failure of at least one prior chemotherapy regimen. It is also indicated for the first-line treatment of patients with locally advanced, unresectable or metastatic pancreatic cancer in combination with gemcitabine. It is administered in tablet form and the recommended dosage for NSCLC is 150 mg/day. For pancreatic cancer, the recommended dosage is 100 mg/day. There are no adequate and well-controlled studies in pregnant women using Erlotinib.

Cetuximab (Erbitux®)

Cetuximab is a chimeric monoclonal IgG antibody produced in mammalian cell culture by mouse myeloma cells and is obtained by attaching the variable regions of the murine monoclonal antibody M225 against epidermal growth factor receptor to constant regions of the human IgG. It is an antineoplastic agent and works by inhibiting the proliferation and inducing apoptosis of human tumor cells that express EGFR. In vitro, cetuximab inhibits the production of angiogenic factors by tumour cells and blocks endothelial cell migration. In vivo cetuximab inhibits expression of angiogenic factors by tumour cells and causes a reduction in tumor neovascularisation and metastasis. Cetuximab is a mediator of antibody dependent cellular cytotoxicity in vitro, targeting cytotoxic immune effector cells towards EGFR expressing tumour cells.

Cetuximab is indicated for the treatment of patients with metastatic colorectal cancer that has been demonstrated to express EGFR and whose disease has progressed or is refractory to irinotecan based therapy. It is indicated for the treatment of patient with locally advanced squamous cell cancer of the head and neck in combination with radiotherapy.

No reproductive toxicology studies of cetuximab have been conducted in animals and data regarding use in pregnant women are not available. Cetuximab is typically administered intravenously once per week. For the treatment of all indications for which it is approved, the initial dose is 400 mg/m² body surface area followed by subsequent weekly doses of 250 mg/m².

Panitumumab (Vectibix™)

Panitumumab consists of 2 gamma (γ) heavy chains and 2 kappa light chains. Panitumumab is a fully human IgG that specifically binds to the EGFR and is produced during recombinant DNA technology in genetically engineered mammalian CHO cells.

Panitumumab is indicated for the treatment of EGFR expressing, metastatic colorectal carcinoma in patients who have disease progression following treatment with fluoropyrimidine, oxaliplatin and irinotecan based chemotherapy.

There are no studies on the use of Panitumumab in pregnant women. It is typically administered intravenously at a dose of 6 mg/kg one every two weeks.

Antimetabolite Drugs

Antimetabolites are drugs that are similar enough to a natural chemical to participate in normal biochemical reactions in the cell but different enough to interfere with normal cellular division and functions of the cell. They are so named because they interfere with the cells' normal metabolic process. Antimetabolites are classified according to the substances with which they interfere.

Examples of antimetabolites suitable for use according to the invention include, but are not limited to methotrexate, 5-fluorouracil, foxuridine, cytarabine, capacetabine, gencitabine, 6-mercaptopurine, 6-thioguanine, cladribine, fludarabine, nelarabine and pentostatin.

Methotrexate

Is an antimetabolite and antifolate drug typically used in the treatment of cancer and autoimmune disease. It acts by inhibiting the metabolism of folic acid. Methotrexate competitively and irreversibly inhibits dihydrofolate reductase (DHFR), an enzyme that participates in tetrahydrofolate synthesis. DHFR catalyses the conversion of dihydrofolate to the active tetrahydrofolate. Folic acid is needed for the de novo synthesis of the nucleoside thymidine, required for DNA synthesis. Also, folate is needed for purine base synthesis. Methotrexate therefore inhibits the synthesis of DNA, RNA, thymidylates and proteins. It acts specifically during DNA and RNA synthesis, and thus it is cytotoxic during the S-phase of the cell cycle. Consequently, it has greater toxic effect on rapidly dividing cells such as malignant and myeloid cells and GI and oral mucosa which replicate their DNA more frequently.

Lower doses of methotrexate have been shown to be very effective for the management of rheumatoid arthritis, Crohn's disease and psoriasis. In these cases, inhibition of dihydrofolate reductase (DHFR) is not thought to be the main mechanism of action, but rather the inhibition of enzymes involved in purine metabolism, leading to the accumulation of adenosine, or the inhibition of T cell activation and suppression of intercellular adhesion molecule expression by T cells (Johnston A et al., (2005) *Clin Immunol* 114:154).

Use of Methotrexate in Pregnancy

Methotrexate is commonly used in combination with misoprostol to terminate early pregnancies. As discussed in the background, is also used to treat ectopic pregnancies. In the case of early missed miscarriage, in which fetal demise has occurred but the body has not expelled the fetus, methotrexate has been used to help the body begin the miscarriage process. Although methotrexate can be given orally, ectopic pregnancy success rates are lower with oral use than with injection. Methotrexate treatment can be given as a single injection or as several injections. Response to methotrexate injection is measured by monitoring β-hCG levels. If an ectopic pregnancy continues after 2 or 3 doses of methotrexate, surgical treatment is necessary to remove the ectopic pregnancy. Methotrexate is also sometimes used following surgical treatment to stop of the growth of any remaining trophoblasts.

Methotrexate therapy is usually considered for ectopic pregnancies that are not too advanced and have not ruptured and provides a treatment option for women concerned with preserving fertility.

Measurement of Beta Human Chorionic Gonadotropin Levels

The measurement and monitoring of β-hCG levels will be familiar to persons skilled in the art of the present invention. The beta subunit of human chorionic gonadotropin can be measured in bodily fluids including urine, serum, blood and cerebral spinal fluid. While not wishing to be bound by theory, measurements of the concentration of β-hCG in a sample are typically analysed at day 4 and day 7 from the initial day (day 1). Since blood levels of β-hCG double about every two to three days, serial testing of β-hCG levels can be used to monitor the efficacy of any treatment regimen. Typically, a reduction of at least 15% of the concentration of β-hCG between days 4 and day 7 is taken to have worked. Usually, β-hCG will be measured until such time as the concentration of β-hCG returns to non-pregnancy levels (<5 international units/L).

Devices for measuring β-hCG in a sample will also be familiar to persons skilled in the art of the present invention. Such means include pregnancy test kits which can be purchased over the counter at pharmacies. These kits are based on a chromatic immunoassay. Alternatively chemiluminescent or fluorimetric immunoassays can be used to quantify β-hCG concentration. Examples of such devices in DELFIA® or autoDELFIA® kits (Perkin Elmer). The devices may be manual or automated.

While not wishing to be bound by theory, diagnosis of ectopic pregnancy is typically carried out by quantitative measurement of the β subunit of β-hCG using any of the methods described above and transvaginal ultrasound. Serum progesterone concentration can also be measured since the corpus luteum appears to secrete less progesterone when an ectopic pregnancy is present compared with a normal pregnancy at similar gestational ages. Typically, a progesterone value of more than 80 nmol/L is associated with a healthy intrauterine pregnancy in 98% of women, whereas a concentration of less than 16 nmol/L is indicative of a non-viable pregnancy, irrespective of location (Stovall T G et al., (1992) *Fertil Steril* 57:456).

It is also possible to image blood flow by transvaginal ultrasonography with colour Doppler flow imaging which can increase the sensitivity and specificity of ultrasonography to diagnose ectopic pregnancy. With an ectopic pregnancy there is a 20% difference in blood flow between the two sides of the pelvis, compared with only an 8% difference with a normal pregnancy.

Dilatation and curettage has been used by some doctors to distinguish an ectopic pregnancy from an intra uterine pregnancy. The procedure is done by dilation of the cervix to allow access of the curette into the uterus. The removed tissue is then examined under the microscope to determine if any embryo-associated tissue is present. If none is seen, it can be presumed that there is no uterine pregnancy, and a diagnosis of ectopic pregnancy can be made and treatment begun.

Cells that Model the Different Layers of the First Trimester Placenta BeWo Cells BeWo cells are a placental cell line that has been widely used as an in vitro model for the placenta, and in particular syncytialised BeWo cells. The cells are originated from a human choriocarcinoma. They are typically used as a model of syncytiotrophoblasts (see FIG. 1).

Syncytiotrophoblasts are multinucleated cells with fused cytoplasm, and form the outermost fetal component of the placenta that abuts maternal tissue. Syncytiotrophoblast tissue have important roles in nutrient exchange/waster disposal, endocrine function (this cell layer is responsible for producing β-hCG), and dampening maternal immune response to prevent rejection.

Cytotrophoblasts are cells that differentiate into syncytiotrophoblasts.

JEG-3 Cells

JEG-3 is a human placental choriocarcinoma cell line. It is commonly used as a trophoblastic model system (see FIG. 1). The cell line is believed to represent the extravillous trophoblast. These are placental cells that are highly proliferative, and are responsible for remodelling maternal tissues (including maternal blood vessels), in order for the placenta to properly implant. They "punch through" the syncytiotrophoblast border, move into the maternal tissues which they then remodel.

JEG-3 cells retain the capacity to produce progesterone, HCG, several steroids and other placental hormones and enzymes and therefore have some properties of syncytiotrophoblasts. The cell line has been extensively used in studies to investigate the regulation by various agents on the proliferation, differentiation and secretion of placenta cells.

Formulations and Dosages

The compositions of the invention will be administered to the subject in a pharmaceutically acceptable form. The term "pharmaceutically acceptable" means approved by a regulatory agency of the Federal or state government or listed in the U.S. Pharmacopeia or other generally recognised pharmacopeia or receiving specific or individual approval from one or more generally recognised agencies for use in animals, and more particularly in humans.

Typically, the composition will be admixed with a pharmaceutically acceptable carrier. As used herein "pharmaceutically acceptable carrier" or "excipient" including, but not limited to any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

Various delivery systems are known and can be used to administer a pharmaceutical composition of the present invention. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it is desirable to administer the EGFR inhibitor and methotrexate according to the dosage and routes of administration as approved by the regulatory authority of each country in which the product is approved for human use. For example, for methotrexate the usual dose range for both oral and subcutaneous administration is 2.5 mg to 50 mg per week, either as a single dose, or in divided doses. For subcutaneous administration, the invention also includes the use of pre-filled syringes.

In another embodiment, the EGFR inhibitor is a monoclonal antibody which is administered to the subject intravenously. The dosage of monoclonal antibody administered to the subject is preferably according to those approved by the appropriate regulatory authority in each country in which the product is approved for human use.

Methods for determining the appropriate dosage for each subject will be familiar to persons skilled in the art of the present invention.

Supplementary active compounds can also be incorporated into the compositions. For example, to limit the side effects methotrexate, the subject may be given folic acid orally daily except on the day they take methotrexate.

Timing and Scheduling of Administration of EGFR Inhibitor and Anti-Metabolite

By way of non-limiting example, the following treatment schedules for the administration of anti-metabolite and EGFR inhibitor are proposed.

Typical treatment schedules for the treatment of ectopic pregnancy are as follows:

Day 0—urinalysis and blood tests to determine β-hCG concentration, a full blood examination, liver function test, and renal function tests.

Day 1—β-hCG concentration measurement and administration of methotrexate intramuscularly or subcutaneously in a single dose.

Day 4—β-hCG concentration measurements.

Day 7—β-hCG concentration measurements, full blood examination, liver function tests, and renal function tests.

Weekly β-hCG concentration measurements until negative (average time is 4 weeks). Avoid pregnancy for three months after methotrexate treatment.

If the β-hCG level on day 7 is at least 15% lower than that on day 4, then the subject undergoes biochemical follow-up.

If the β-hCG level on day 7 is the same or higher than that on day 4, the subject receives a second dose of methotrexate.

Follow-up β-hCG tests are typically performed weekly until they are negative (≤5 IU/L).

In another embodiment, the same treatment schedule is followed however the methotrexate injection is substituted with an oral dosage form of methotrexate.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or groups of elements or integers.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All documents referred to in this specification are deemed to be incorporated by reference in their entirety.

The invention is hereinafter described by way of the following non-limiting Examples and with reference to the accompanying Figures.

EXAMPLE 1

Methods

Cell Culture.

JEG-3 and BeWo cells were cultured in DMEM/F-12 medium containing L-glutamine (Invitrogen) supplemented with 10% fetal calf serum (ICP Biologicals). For treatments with methotrexate (Sigma) or Gefitinib (LC Laboratories) media was replaced with media containing 1% FCS.

Immunohistochemistry on Xenograft Sections.

Paraffin sections were cut, dewaxed in xylene and rehydrated before blocking endogenous peroxidase with Peroxo-Block (Invitrogen). A protein block (Dako) was performed prior to overnight incubation with syncytin mouse monoclonal antibody (clone 4F10, Sapphire Biosciences) or Ki67 (Invitrogen) followed by detection using the SuperPicture Polymer Detection Kit (Invitrogen).

Human Tissue Collection and Isolation of Primary Cytotrophoblast.

Fallopian tube biopsies were collected from the ectopic implantation site from participants (aged 18-45) at the time of surgery (n=5). Biopsies were fixed in 4% neutral-buffered formalin overnight at 4° C. followed by storage in 70% ethanol, and subsequent embedded in paraffin wax for immunohistochemistry. Ethical approval for this study was obtained from the Lothian Research Ethics Committee.

$1^{st}$ trimester placenta was collected from healthy women undergoing elective termination of pregnancy (amenorrhea: 8-10 weeks). This research protocol, including written consent from patients, was approved by the Southern Health Human Research and Ethics Committee. From the $1^{st}$ trimester placental tissue, primary cytotrophoblast was isolated as previously described (Cartwright J E et al., (2002) *Placenta* 23:232-235). The inventors confirmed the purity of primary cytotrophoblast cells by immunocytochemistry for cytokeratin 7 as previously described (Paiva P et al., (2007) *Endocrinology* 148:5566-5572).

Immunohistochemistry of Tubal Implantation Sites for EGFR.

3 μm paraffin sections of Fallopian tube were cut, dewaxed in xylene, rehydrated and subjected to antigen retrieval by pressure cooking in sodium citrate before blocking endogenous peroxidase with 3% hydrogen peroxidase (Sigma-Aldrich). An avidin-biotin block (Vector Laboratories) and protein block (Dako) were performed prior to overnight incubation with EGFR mouse monoclonal antibody (Novo-Castra) followed by biotinylated secondary horse anti-mouse antibody and ABC-Elite (Vector Laboratories). Positive immunostaining was visualized using 3,3-diaminobenxidine (Vector Laboratories).

Western Blot Analysis of EGFR.

Cells were trypsinised, washed and lysed in RIPA buffer (50 mM Tris, 150 mM NaCl, 1% triton, 0.1% SDS, 1 mM EDTA, 0.1% sodium deoxycholate, protease inhibitor cocktail, sodium vanadate) for 10 min prior to 15 min sonication and centrifugation at 4° C. to remove cellular debris. Lysates were resolved by reducing SDS-PAGE and transferred to PVDF membranes using the iBlot dry transfer system (Invitrogen). Anti-pY845 EGFR rabbit polyclonal antibody (Invitrogen) was used to detect phosphorylated EGFR and anti-C-terminal EGFR rabbit polyclonal antibody 1005 (Santa Cruz) was used to detect total EGFR.

In Vitro Cell Viability Assay.

Viability was analysed using the CellTiter-Blue® Cell Viability Assay (Promega).

xCELLigence Real-Time Analysis.

The Real-Time Cell Analyzer (RTCA) SP instrument (Roche Diagnostics GmbH) was placed in a humidified incubator maintained at 37° C. with 5% $CO_2$. Cells were seeded at 625-40,000 cells per well in 96-well plates (E-plate 96, Roche Diagnostics GmbH) in medium containing 1% or 10% serum. Cells were initially monitored once every 2 min for 1 h and then once every hour. After addition of treatment, cells were monitored once every 10 min for 3 h and thereafter once every hour.

Bio-Plex Analysis.

Cell lysates were analyzed for levels of phosphorylated Akt, p-38 MAPK, IκB-α or Erk1/2 using the Bio-Plex Phosphoprotein Assays (Bio-Rad Laboratories).

Apoptosis Assay.

Cell suspensions were fixed in ice-cold methanol overnight at −20° C., washed in PBS and stained with M30 CytoDeath mouse monoclonal antibody (Sapphire Biosciences), followed by ALEXA® 488-conjugated anti-mouse antibody (Invitrogen). Samples were analyzed on a BD FACS Canto II analyser (BD Biosciences).

Gene Expression Analysis.

RNA was extracted from cells using RNeasy Mini Kit (Qiagen). First strand cDNA was synthesised using 250 ng of total RNA, Superscript III and random hexamers (Invitrogen). Quantitative real-time PCR analysis was performed on the ABI 7900HT Real-Time PCR system (Applied Biosystems). Gene expression analysis was performed using commercially available TaqMan® Gene Expression Assays (Applied Biosystems). The relative expression was calculated by normalizing to GAPDH and the fold expression change for each gene in cells treated with the drugs relative to untreated cells was determined by the expression $2-\Delta\Delta CT$.

Mouse Model.

5- to 6-week-old female SCID mice (C.B-17-Igh-$1^b$-Prkdc$^{scid}$; Animal Resources Centre, Perth, Australia) were inoculated with JEG-3 cells ($10^6$ in 100 μL PBS) subcutaneously. Mice were treated starting at day 7 after JEG-3 injection with gefitinib (0.5-2 mg per dose in 50 μL DMSO), methotrexate (0.04-0.4 mg per dose in 100 μL buffer) or respective vehicle (DMSO/buffer) per intraperitoneal injection (i.p.). Xenograft volume in cubic millimeters was determined using the formula (length×width$^2$)/2, where length was the longest axis and width was the measurement at right angles to the length. The mice were sacrificed after 19 days, at which time we excised the xenografts, weighed and measured them, and collected blood by cardiac puncture. hCG was quantified in mouse serum using the Elegance hCG ELISA assay (Bioclone). The animal study was reviewed and approved by the Monash University Animal Welfare Committee.

Statistical Analyses.

The inventors used a one-way or two-way analysis of variance (ANOVA) followed by Bonferroni post test for comparison between more than two groups. P<0.05 was considered significant. All values are expressed as means±s.e.m.

EXAMPLE 2

In Vitro Model for Efficacy Testing of Methotrexate and EGFR as Single Agents and in Combination on Placenta-Derived Tissue Two different placenta-derived trophoblast-like human choriocarcinoma cell lines as well as isolated human first trimester extravillous trophoblast cells were incubated with methotrexate±gefitinib at various concentrations for 72 hours. The placenta-derived choriocarcinoma cell lines tested were JEG-3 cells which are cytotrophoblast-like cells and BeWo cells which can be syncytialised upon stimulation with the cAMP-inducer forskolin and may hence represent the syncytiotrophoblast cell population. The viability of the JEG-3, BeWo and primary first trimester extravillous trophoblast cells after treatment with methotrexate and gefitinib was assessed by the CellTiter-Blue® Cell Viability Assay.

JEG-3, BeWo and primary first trimester trophoblast cells were seeded at 5000 cells per well in 96-well plates in DMEM/F-12 culture medium containing 1% foetal bovine serum and 1% penicillin/streptomycin and incubated at 37° C. in a humidified atmosphere of 5% $CO_2$. Approximately 40 hours after seeding, drugs were added to the cells in DMEM/F-12 containing 1% foetal bovine serum. A dose of 100 μM of methotrexate (JEG-3 and primary first trimester trophoblast cells) and 200 μM of methotrexate (syncytialised BeWo cells) was used because this dose decreased cell viability by approximately 50%, as observed in initial dose-response experiments. Cells treated with vehicle (DMSO) served as control cells. In all figures, data are expressed as means±SEM. One-way ANOVA and Student's t test were used to compare means between experimental groups. Statistical significance was assumed at P values<0.05. All experiments have been repeated at least twice.

Figure 2:
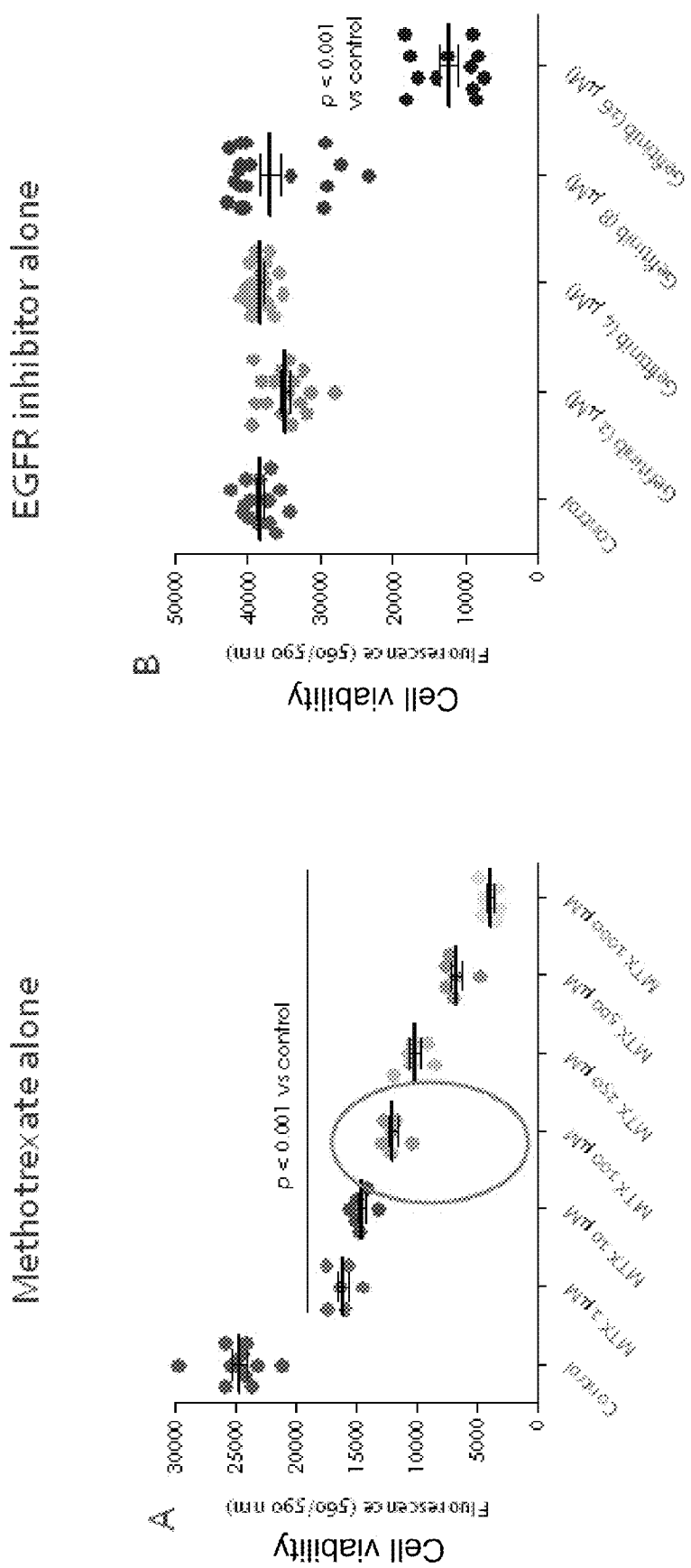
FIG. 2 shows the effect of methotrexate alone (A) or gefitinib alone (B) or the combination of methotrexate and gefitinib (C) on the cell viability in vitro of trophoblast JEG-3 cells.
Figure 2C:
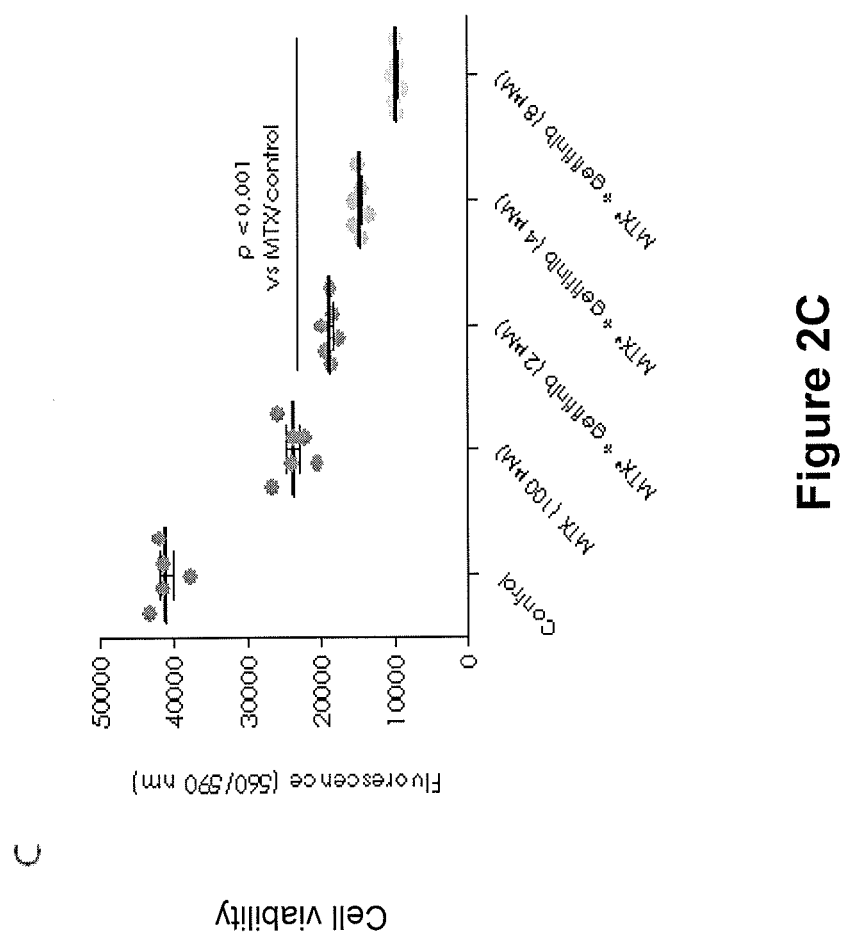

Efficacy of either methotrexate (FIG. 2A) or gefitinib (FIG. 2B) on cell viability of JEG-3 cells was determined at 72 hours. The combined addition of methotrexate and gefitinib is shown in FIG. 2C. The combination of the two agents caused a significant supra-additive effect on JEG-3 cell viability compared with either agent alone. n=6 biological replicates per experimental group.

Figure 3:
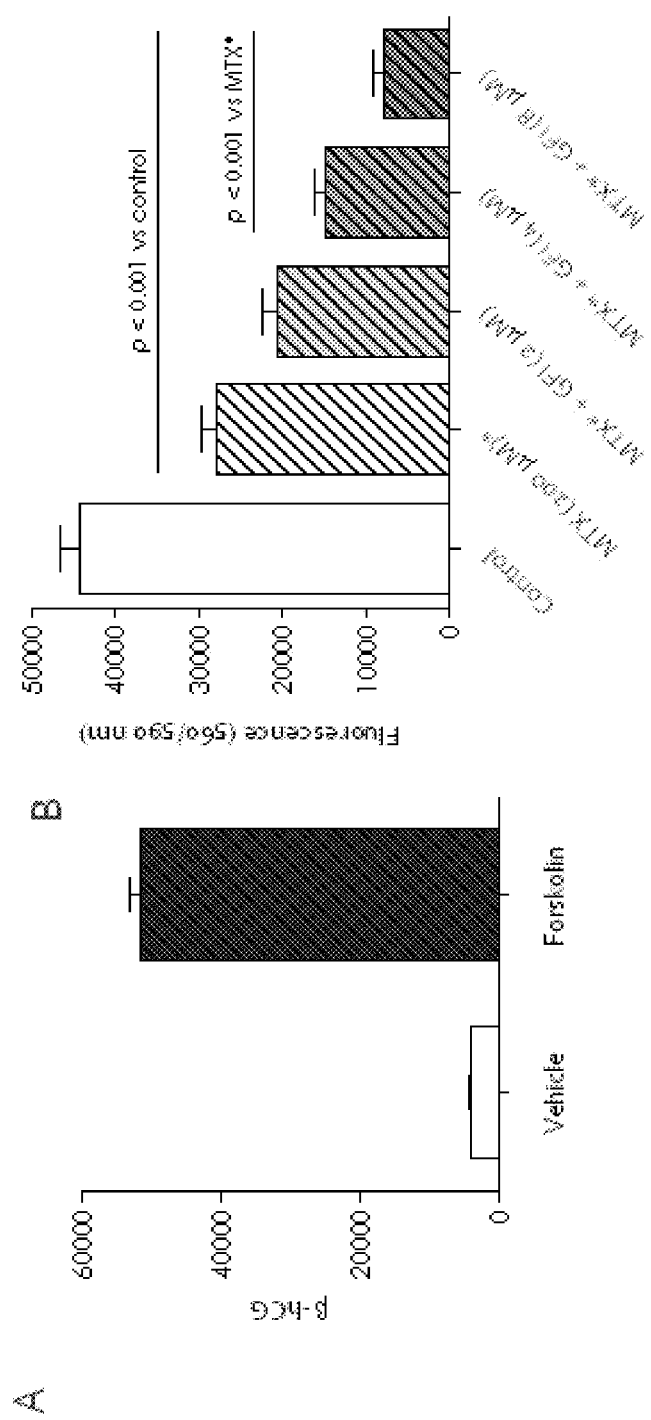
FIG. 3 (A) shows the levels of β-hCG secreted by vehicle- and forskolin-treated BeWo cells, where increased levels of β-hCG with forskolin treatment, is a marker for syncytialisation. (B) shows the effect of methotrexate alone and in combination with gefitinib on cell viability in vitro of syncytialised (forskolin-treated) BeWo cells.

The effect of combined addition of methotrexate and gefitinib on cell viability of syncytialised BeWo cells is shown in FIG. 3. BeWo cells were seeded as described above and treated with forskolin or vehicle (DMSO) for 48 hours to induce syncytialisation. Syncytialisation of forskolin-treated cells was confirmed by increased β-hCG levels in conditioned medium (see FIG. 3A) and immunohistochemical staining for E-cadherin (not shown). Methotrexate and gefitinib were administered to syncytialised (forskolin-treated) BeWo cells and cell viability determined after 72 hours by CellTiter-Blue assay. As demonstrated in FIG. 3B, the combination of methotrexate and gefitinib caused a significant supra-additive effect on cell viability compared with either agent alone. The combination of agents was found to be statistically significant over vehicle-treated control cells and over the use of methotrexate as single agent (p<0.001). n=6 biological replicates per experimental group.

Figure 4:
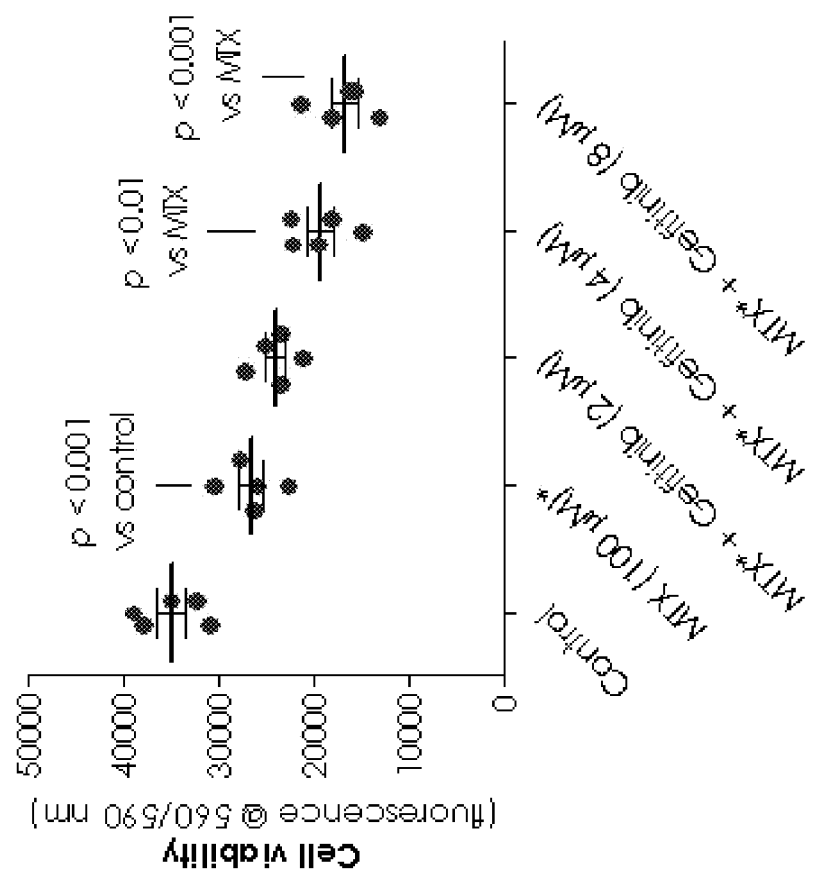
FIG. 4 shows the effect of methotrexate alone and in combination with gefitinib on cell viability in vitro of primary first trimester extravillous trophoblast cells.

Importantly, the efficacy of methotrexate±gefitinib was also assessed in primary human extravillous trophoblast cells isolated from first trimester placenta. FIG. 4 shows the effect of combined addition of methotrexate and gefitinib on primary human trophoblast cell viability, as assessed 72 hours after addition of drugs by CellTiter-Blue assay. Just as demonstrated in FIGS. 2C and 3B, the combination of the two agents caused a statistically significant supra-additive effect on cell viability compared with methotrexate as a single agent and with vehicle (DMSO)-treated control. n=5 biological replicates per experimental group.

EXAMPLE 3

EGFR Expression in Placental Tissue

Figure 5:
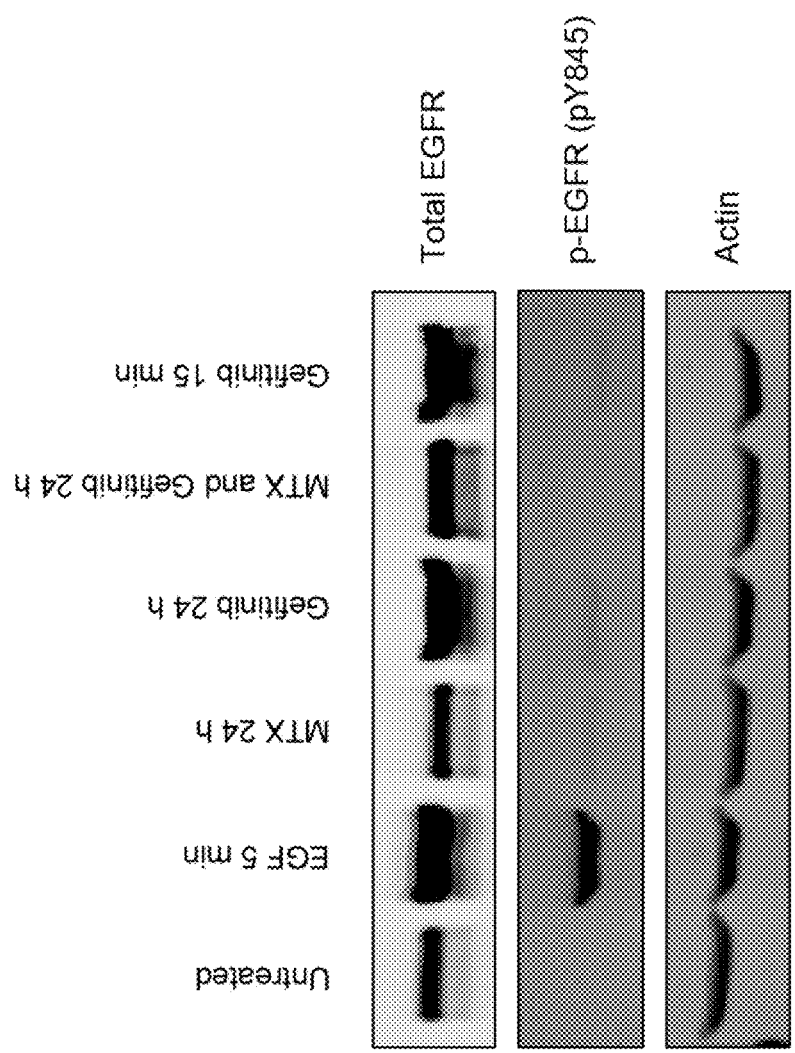
FIG. 5 shows Western blot to demonstrate the effects of pre-treatment with methotrexate (MTX)±gefitinib on EGF induced EGFR phosphorylation of JEG3 cells. Time shown is period of pre-treatment. EGF was added to all groups except untreated. Results are representative of three independent experiments.

EGFR expression was examined in an ectopic pregnancy specimen. Strong expression of EGFR was found in particular on the syncytiotrophoblast and cytotrophoblast cells. It was also confirmed that EGFR was highly expressed on various placental cell types such as JEG3 cells (FIG. 5), syncytialised BeWo cells and first trimester placenta. Pre-incubation of JEG3 cells with gefitinib±MTX potentially abolished EGF induced EGFR phosphorylation. MTX alone also partially inhibited EGF induced EGFR phosphorylation. It was concluded that there is strong EGFR expression on placental cells, including those from ectopic pregnancies.

EXAMPLE 4

Figure 6A:
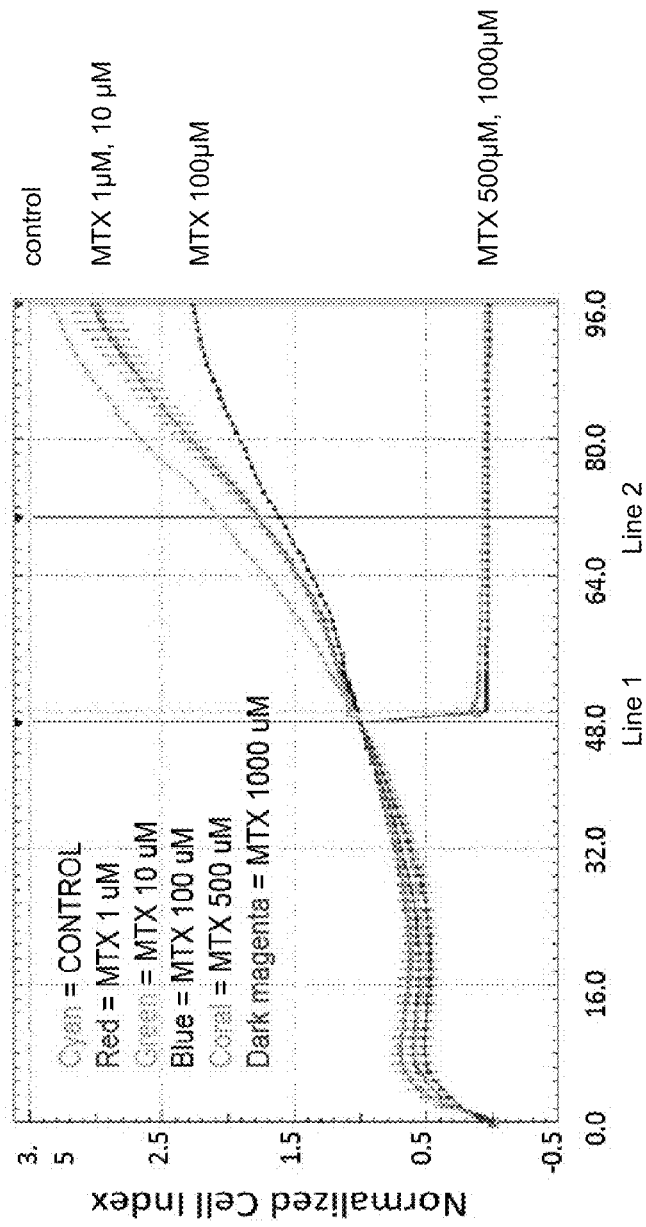
FIG. 6 shows combination methotrexate (MTX) and gefitinib is supra-additive in killing placental cells in vitro. Effects of MTX alone (a), gefitinib alone (b) and combination treatment (c) on JEG3 cell growth over time, measured using the xCELLigence® System. Line 1—shows the time that the treatments were given. Line 2—shows the readout 24 hours after incubation with treatments. Mean of triplicates±S.E.M. shown.
Figure 6B:
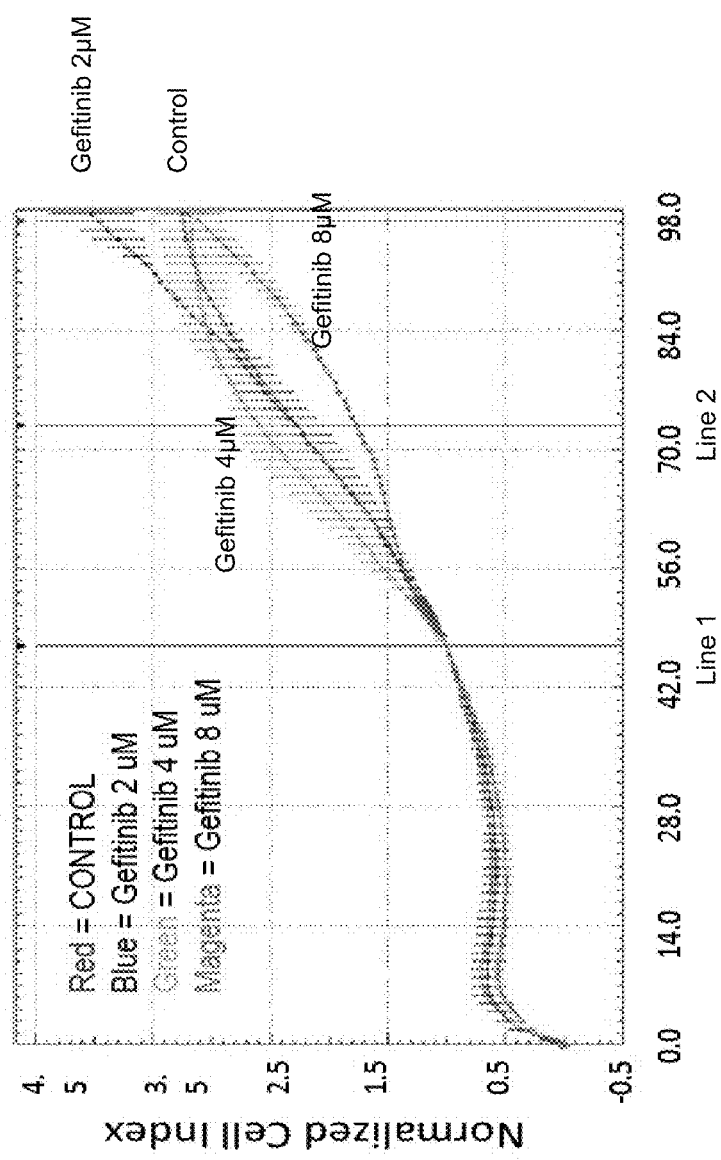
Figure 6C:
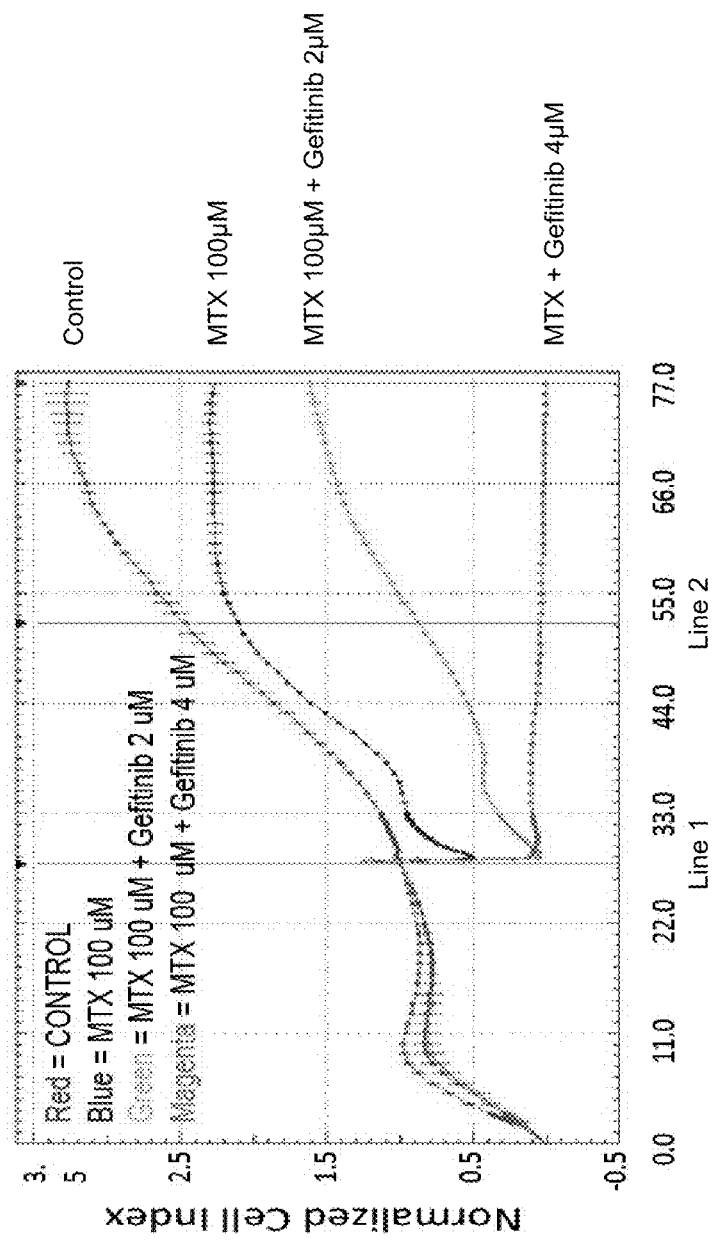

In Vitro Model for Efficacy Testing of Methotrexate and Gefitinib on Placental Cells The ability of gefitinib and MTX to kill placental cells was examined using the xCELLigence System. This assay measures electrical impedance across cells, with more cells increasing impedance. By taking continuous measurements, this assay also tracks cell growth longitudinally. MTX alone resulted in decreased JEG3 cell growth in a dose dependent manner (FIG. 6A) whereas gefitinib caused either no (2 or 4 µM), or a small and transient (8 µM) decrease in JEG3 growth (FIG. 6B). However, when these same gefitinib doses were added to a fixed dose of MTX, a potent and supra-additive effect was observed, with cell death occurring quickly after drug administration (FIG. 6C).

Figure 7:
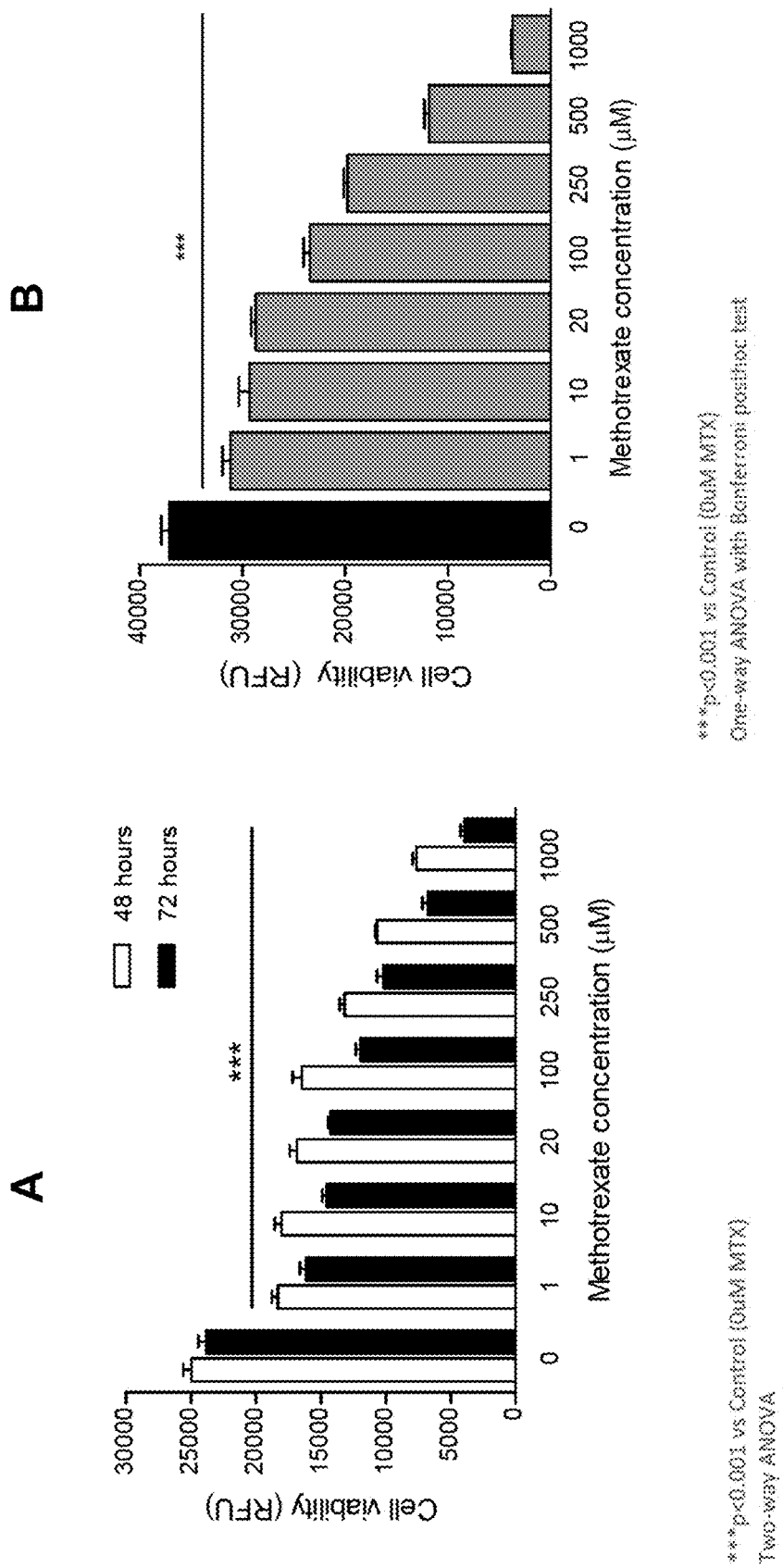
FIG. 7 shows single agent methotrexate (MTX) but not gefitinib kills JEG3 cells in a dose response manner by both 48 and 72 hours. (A,B) Effects of MTX treatment on viability of (A) JEG3 or (B) syncytialised BeWo cells. Mean±S.E.M. shown. All results are representative of at least two independent experiments (n≥5 per group in each experiment). Groups in A were analysed with a Two-way Anova, Groups in B were analysed with a One-way Anova with Bonferroni posthoc test.***P<0.001 vs control.

The above findings were verified with a fluorescence-based end point assay (CellTitre Blue) using different placental cell types. MTX treatment resulted in death of both JEG3 (FIG. 7A) and BeWo cells (FIG. 7B) in a dose dependent manner.

Figure 8:
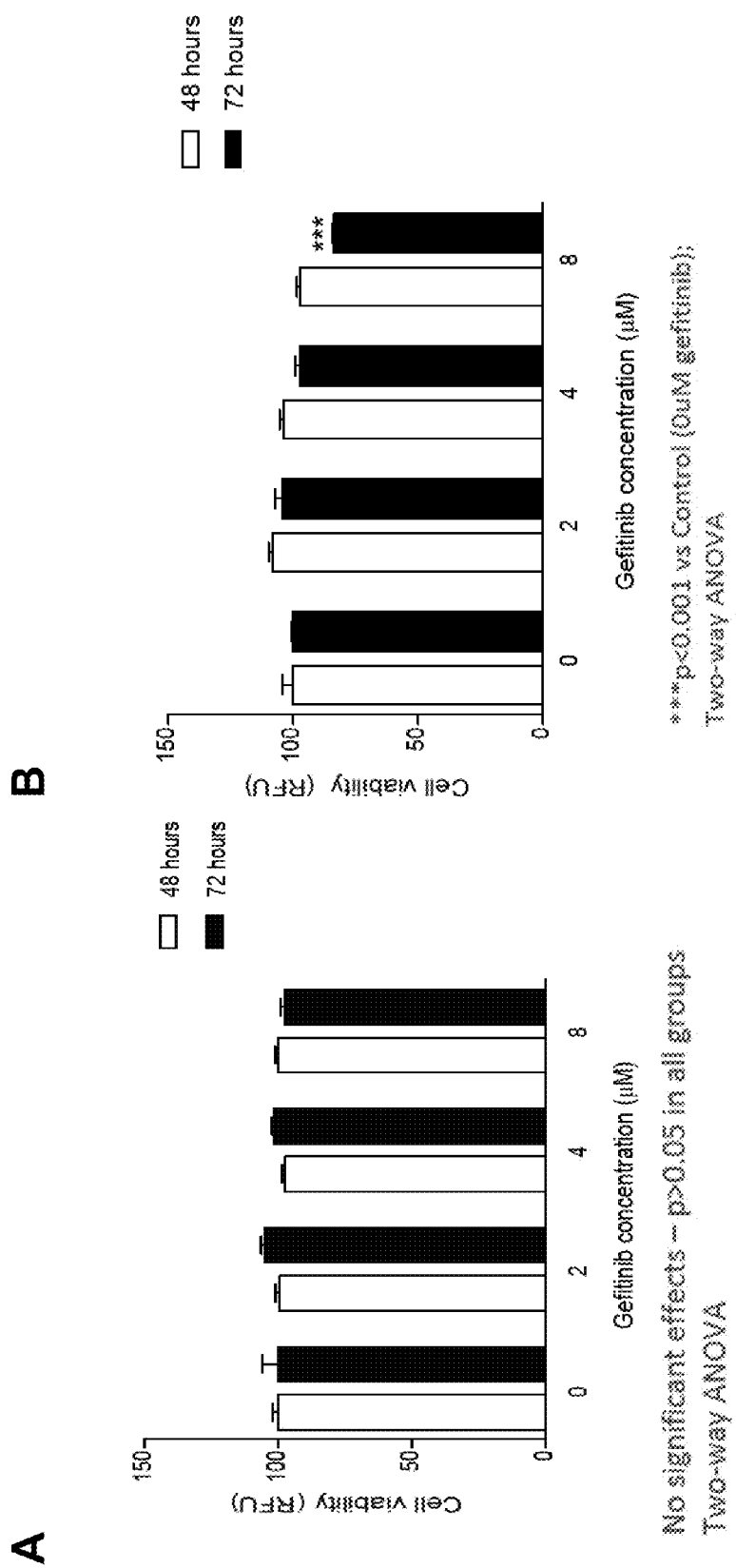
FIG. 8 Effects of gefitinib treatment on (A) JEG3 or (B) syncytialised BeWo cells. Mean±S.E.M. shown. All results are representative of at least two independent experiments (n≥5 per group in each experiment). Groups were analysed with two-way ANOVA: ***P<0.001 vs control (0 µM gefitinib).
Figure 9A:
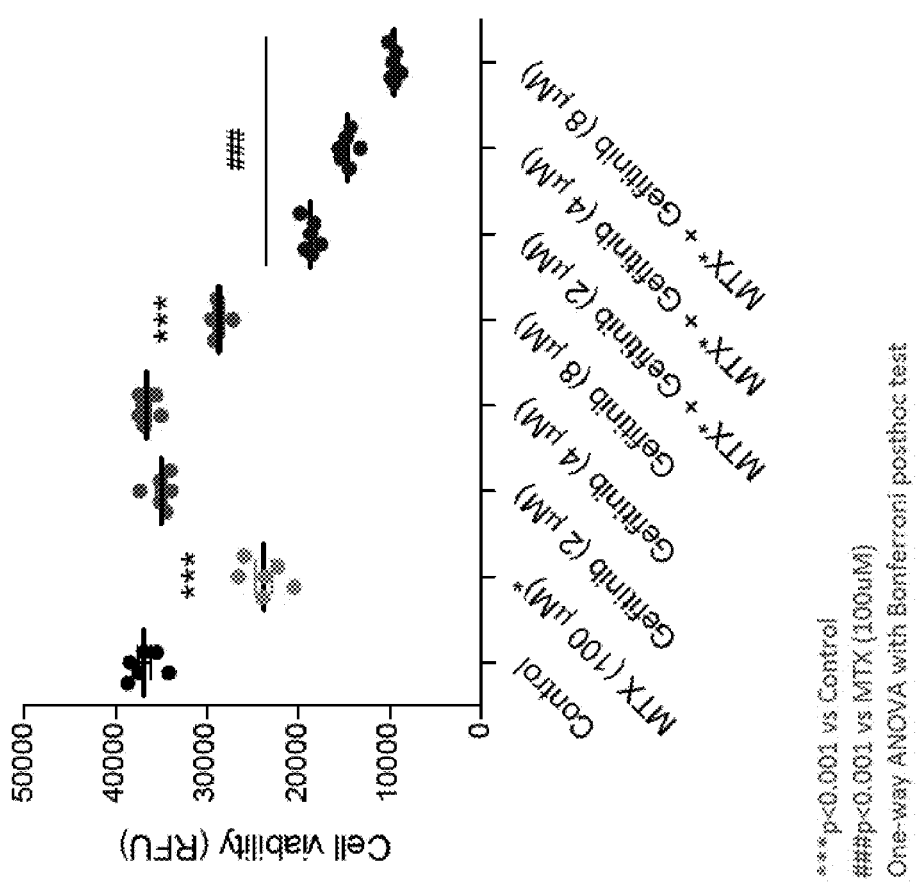
FIG. 9 Effects of 48 hours of 100 µM MTX±gefitinib treatment on the viability of JEG3 (A) syncytialised BeWo (B) and primary $1^{st}$ trimester trophoblast cells (C and D). Results are representative of at least two independent experiments (n≥5 per group in each experiment). Mean±S.E.M. shown for all graphs. Groups were analysed with one-way ANOVA with Bonferoni post hoc test: *P<0.05 vs control, P<0.01 vs control, *P<0.001 vs control. #P<0.05 vs MTX, ##P<0.01 vs MTX, ###P<0.001 vs MTX, ≠≠P<0.01 vs MTX (100 µM).
Figure 9B:
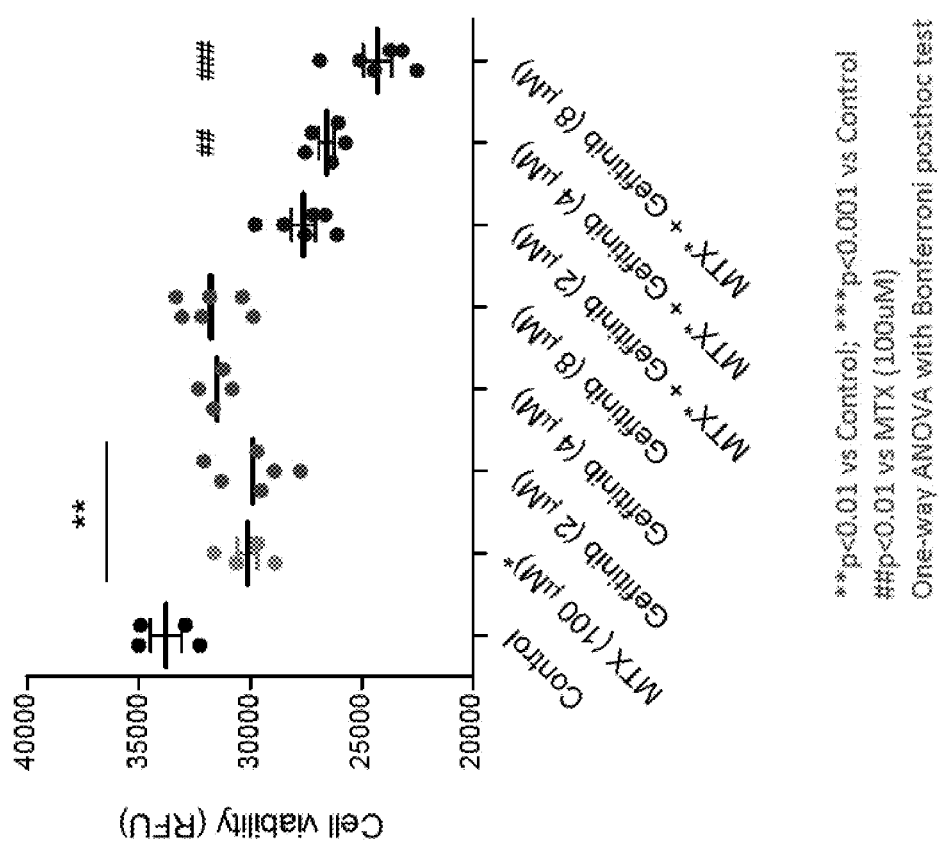

Gefitinib alone caused little or no cell death in either of these cell lines, even at increasing doses (FIGS. 8A & B). However, when MTX was given at a fixed concentration, the addition of gefitinib caused potent JEG3 (FIG. 9A) and BeWo (FIG. 9B) cell death in a dose dependent manner.

Figure 9C:
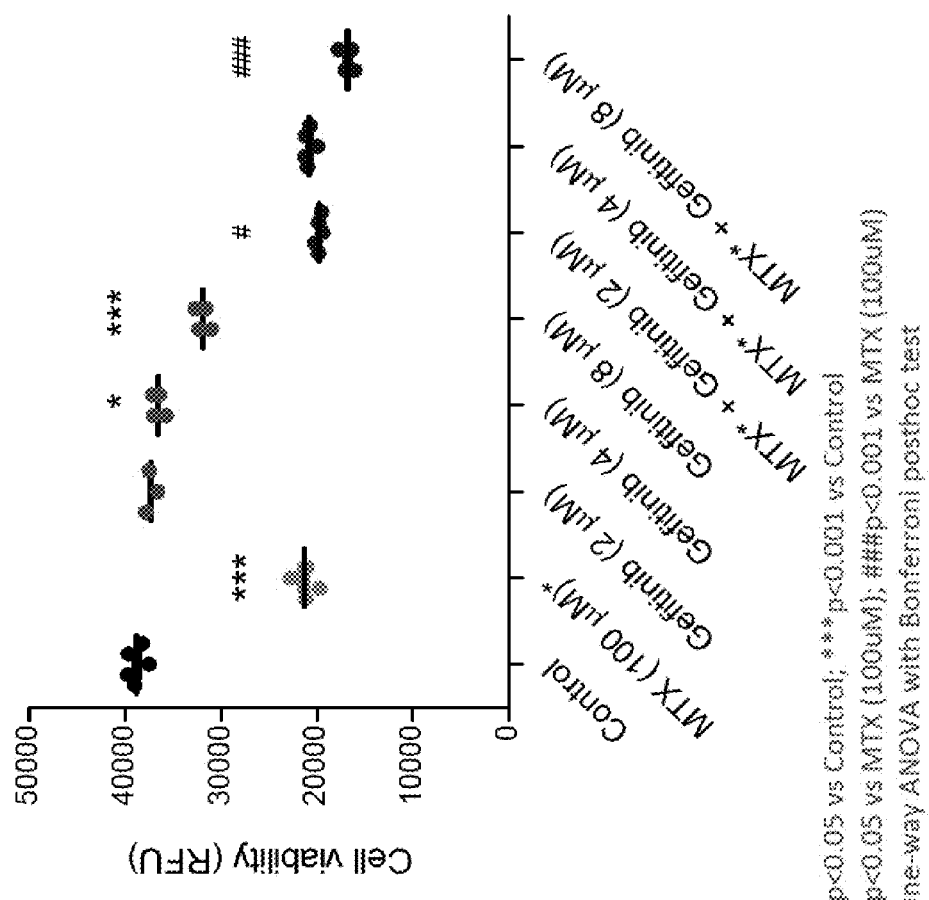
Figure 9D:
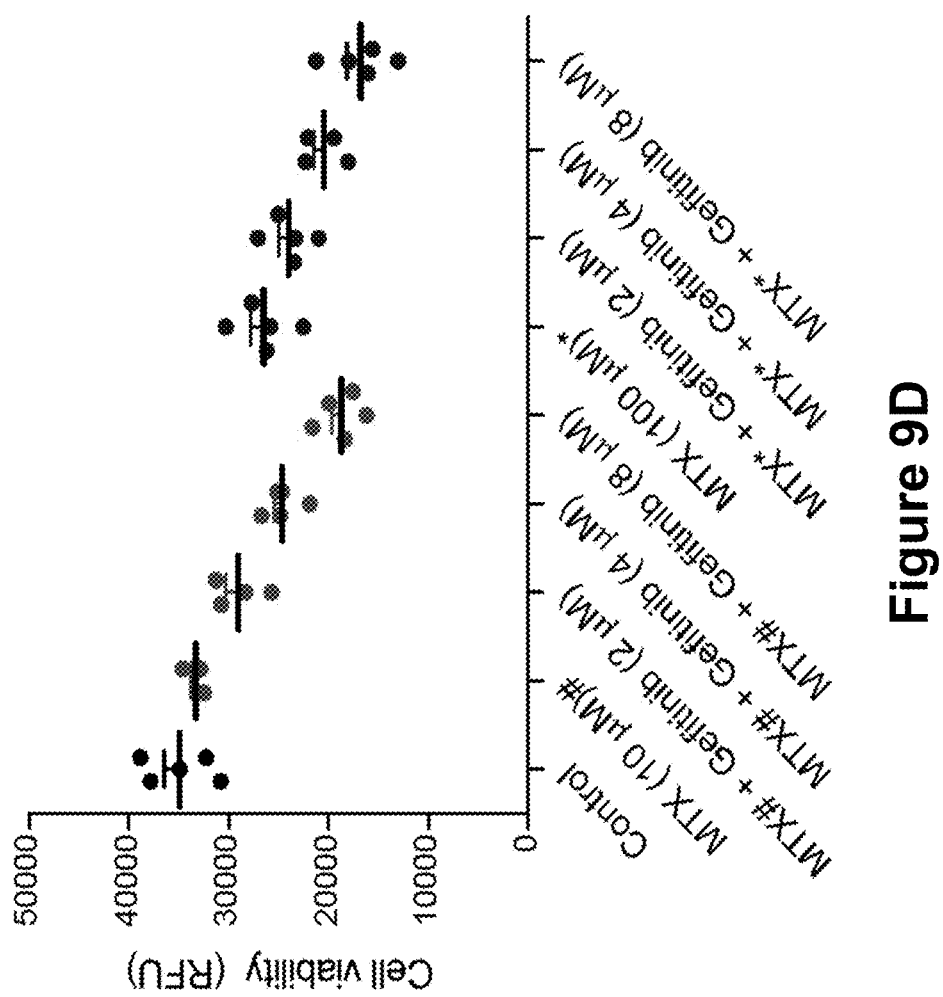

Combination treatment also induced greater cell death compared to either agent alone in primary first trimester extra-villous trophoblast (FIG. 9C), with cell death caused by the addition of gefitinib being dose dependent (FIG. 9D).

From this data it was concluded that the combination of MTX and gefitinib is supra-additive in inducing placental cell death in vitro.

EXAMPLE 5

In Vivo Model for Efficacy Testing of Methotrexate and EGFR as Single Agents and in Combination on Tumour Volume The ability of MTX and gefitinib to decrease tumour volume of subcutaneous JEG3 xenografts in SCID mice was examined. This model was developed by the inventors since there are no established in vivo models of ectopic pregnancies, an almost uniquely human disease.

A subcutaneous JEG-3 xenograft model as established in SCID mice where $1 \times 10^6$ JEG-3 cells were injected into the flanks of mice. The JEG3 xenografts grew rapidly and by day 19, there was evidence of significant proliferation (Figure not shown), lacunar lakes at the periphery, consistent with vascular remodeling induced by invading placental tissues, and seen at the site of ectopic pregnancies, and syncytin expression (human placental protein).

Figure 10:
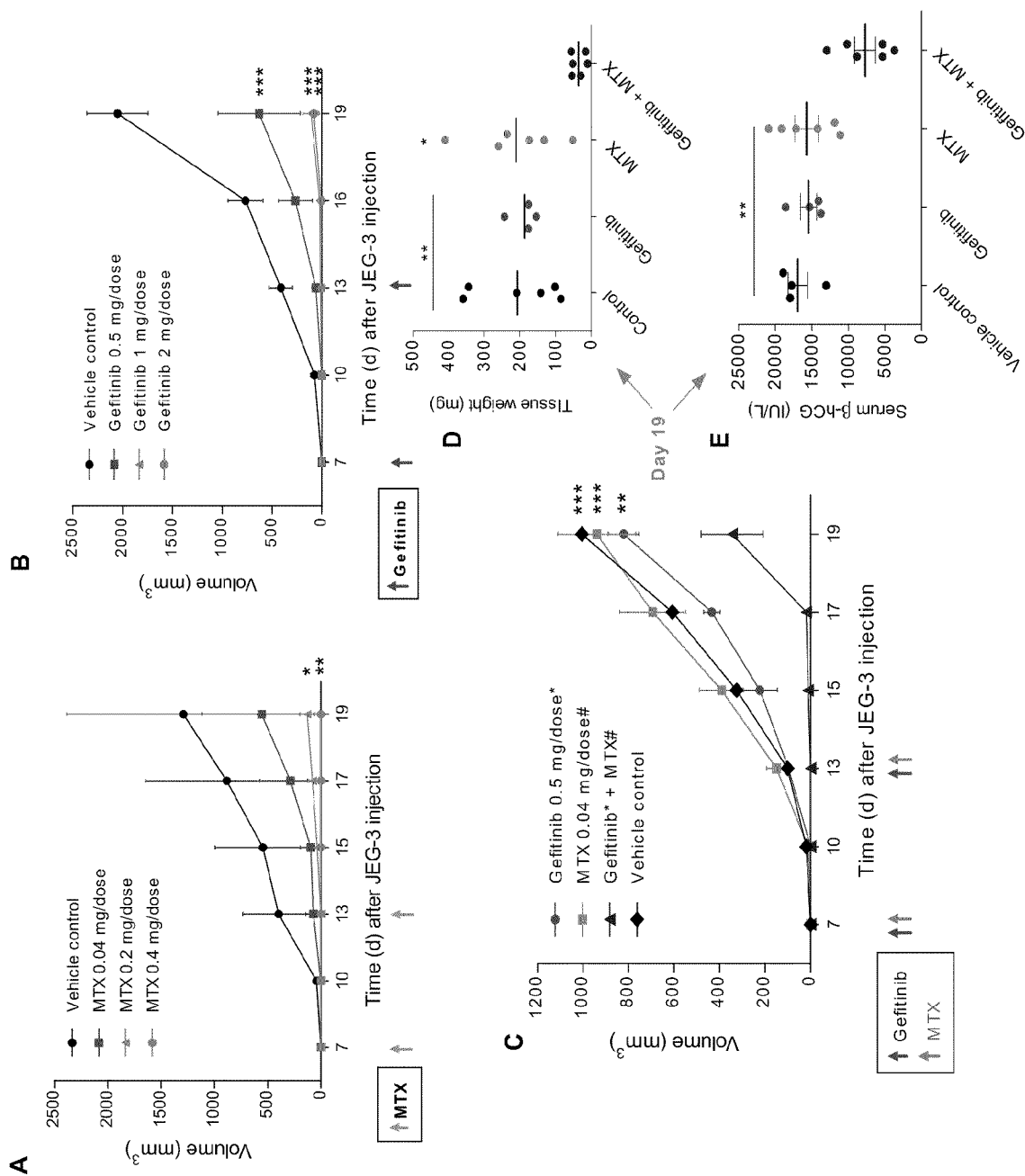
FIG. 10 Methotrexate (MTX) and gefitinib regresses subcutaneous (s.c.) JEG3 xenografts in vivo, and are more potent when combined. JEG3 s.c. xenograft volume after intraperitoneal (i.p.) administration of different doses of MTX (A) and gefitinib (B) JEG3 xenograft volume (C), xenograft tissue weights (D) and serum hCG levels (E) after i.p. injection of MTX or gefitinib alone, and MTX±gefitinib. For all experiments shown, n≥5 SCID mice were used per group, with treatments given at days 7 and 13 after s.c. injection of JEG3 cells. Control for (C) was the vehicle for both MTX and gefitinib. In Figures A, B, comparisons were made to vehicle control. In figures C, D, E, comparisons were made with combination MTX and gefitinib. Mean±S.E.M. shown. Groups were compared using two-way ANOVA, where differences at each time point were compared: *P<0.05, P<0.01, *P<0.001.

As shown in FIG. 10A, mice (n=5 per experimental group) were injected intraperitoneally with either vehicle control (carbonate buffer) or various doses of methotrexate on days 7 and 13 post JEG-3 cell injection. Once palpable, xenograft growth was monitored by measuring tumour length and width every 3 days using digital callipers. Tumour volume in mm³ was determined using the formula (length×width)/2, where length was the longest axis and width being the measurement at right angles to the length. Data are expressed as average tumour volume±SEM for each treatment group.

As shown in FIG. 10B, the same protocol as that for methotrexate administration was followed, however instead of methotrexate, the mice (n=5 per group) were injected intraperitoneally with either vehicle (DMSO) or gefitinib at various doses on days 7 and 13. Mean tumour volume was monitored by digital calliper measurements every 3 days. Tumour volume was determined as described above.

Figure 11:
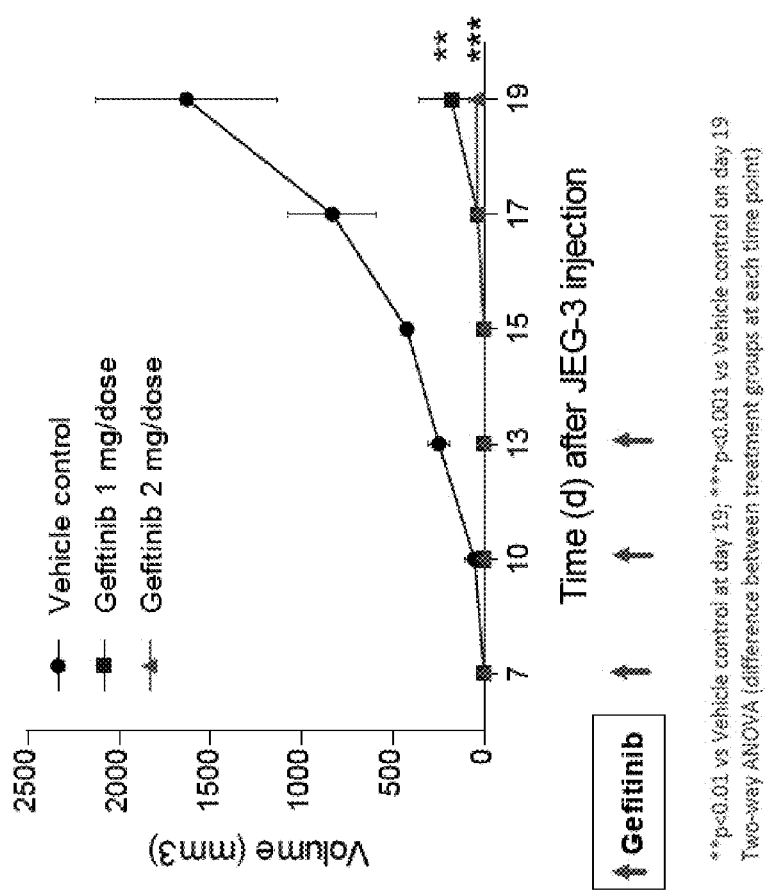
FIG. 11 JEG3 subcutaneous (s.c.) xenograft volume after intraperitoneal administration of three doses of gefitinib. n=3 SCID mice used per group, with treatments given at days 7, 10 and 13 after s.c. injection of JEG3 cells. Groups were compared with two-way ANOVA: P<0.01 vs vehicle control, *P<0.001 vs vehicle control, # P<0.05 vs MTX.

As shown in FIG. 10A, a decrease in xenograft tumour volume was observed with increasing doses of MTX. In contrast to the in vitro assays where gefitinib alone caused little or no cell death, single agent gefitinib in vivo resulted in potent dose dependent reductions in tumour volume (FIG. 10B and FIG. 11).

The inventors then examined whether combining the two drugs (MTX and gefitinib) would result in further reductions of tumour size. To do this, the inventors chose doses of MTX (0.04 mg/dose) and gefitinib (0.5 mg/dose) where some reduction of xenograft tumour volume was observed (FIGS. 10A & 10B), but they were still large enough to examine for the possibility of further reductions in size when the treatments were combined.

In combination (n=7 mice), methotrexate and gefitinib acted in a supra-additive manner to significantly inhibit placenta-derived tissue xenograft growth compared with single agent treatment (n=5 mice per treatment group) and/or vehicle control (n=7 mice). Mice that were given both methotrexate vehicle (carbonate buffer) and gefitinib vehicle (DMSO) served as vehicle controls.

Indeed, it was found that combination treatment potently decreased xenograft tumour size (FIG. 10C) and weight (FIG. 10D) compared to either agent alone.

The inventors measured hCG in serum collected at the time of sacrifice (FIG. 10E) since this is used clinically as a blood biomarker to assess the size of ectopic pregnancies. They found a significant decrease in serum hCG levels with combination treatment compared to single agents. It was concluded that the combination of gefitinib and MTX can potently regress placental cells in an in vivo model.

The data presented herein demonstrate that blocking EGFR signalling has a significant negative impact on placental tissues either alone or in combination with methotrexate. When combined treatment was used, the effects on trophoblast cell viability were supra-additive in both the in vitro and in vivo setting.

EXAMPLE 6

Examination of Mechanism of Action

To further explore how these drugs may be acting together to enhance placental cell death, the inventors investigated the phosphorylation status of Akt, p38 mitogen-activated protein kinase (p38-MAPK), extracellular signal-regulated kinase 1/2 (ERK1/2) and IKappaB Kinase (IKB) in response to various treatments in JEG3 cells. These are key signaling molecules representing major downstream pathways of EGFR (Dutta PR & Maity A (2007) Cancer Lett 254:165-177).

Figure 12A:
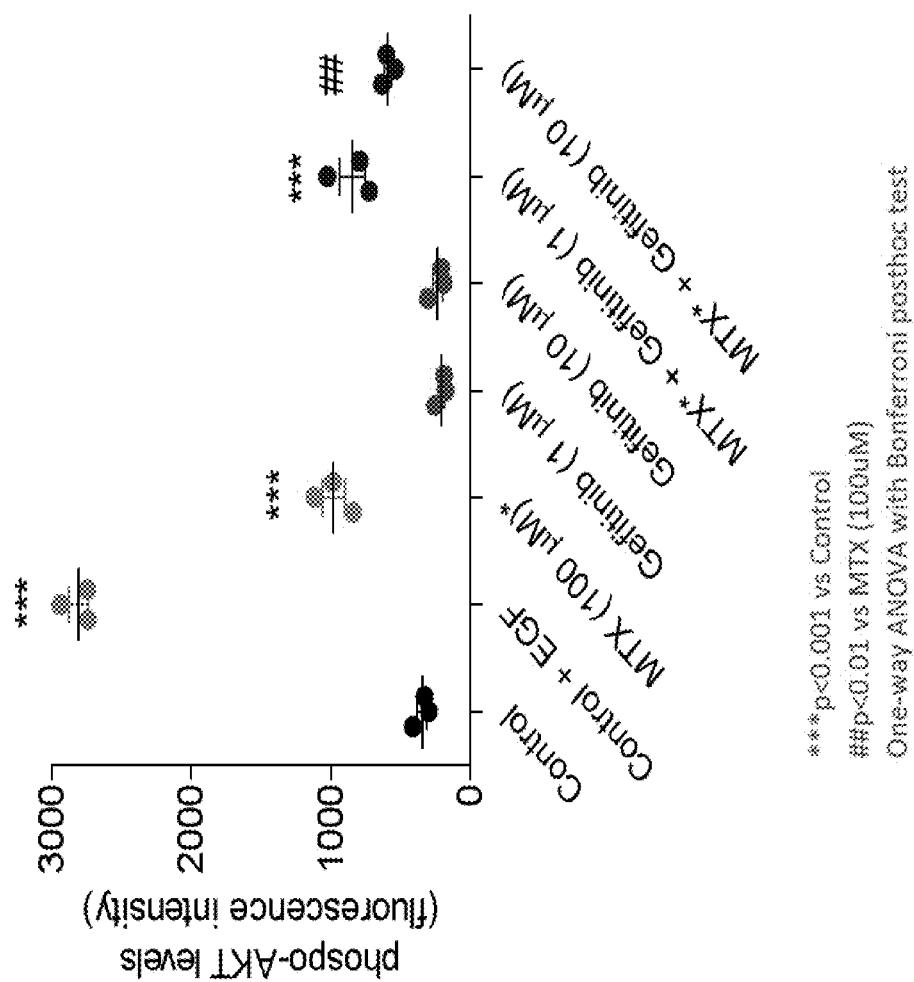
FIG. 12 EGF induced phosphorylation of molecules downstream to EGFR is blocked by methotrexate (MTX)±gefitinib. Phosphorylated Akt levels after treatment of JEG3 cells with MTX±gefitinib (A). Phosphorylated (B) p38 MAPK, (C) ERK1/2 and (D) IKB-α in JEG3 cells after treatment with MTX±gefitinib. All groups were treated with EGF, except 'control'. Mean of triplicates±S.E.M. shown for all results. Comparisons were done using one-way ANOVA with Bonferroni post hoc test (A) or Two way ANOVA (difference between treatment groups at each time point): ≠P<0.05 vs gefitinib at 8 µM concentration, P<0.01 vs control, *P<0.001 vs control, ##P<0.01 vs MTX, ###P<0.001 vs MTX.
Figure 12B:
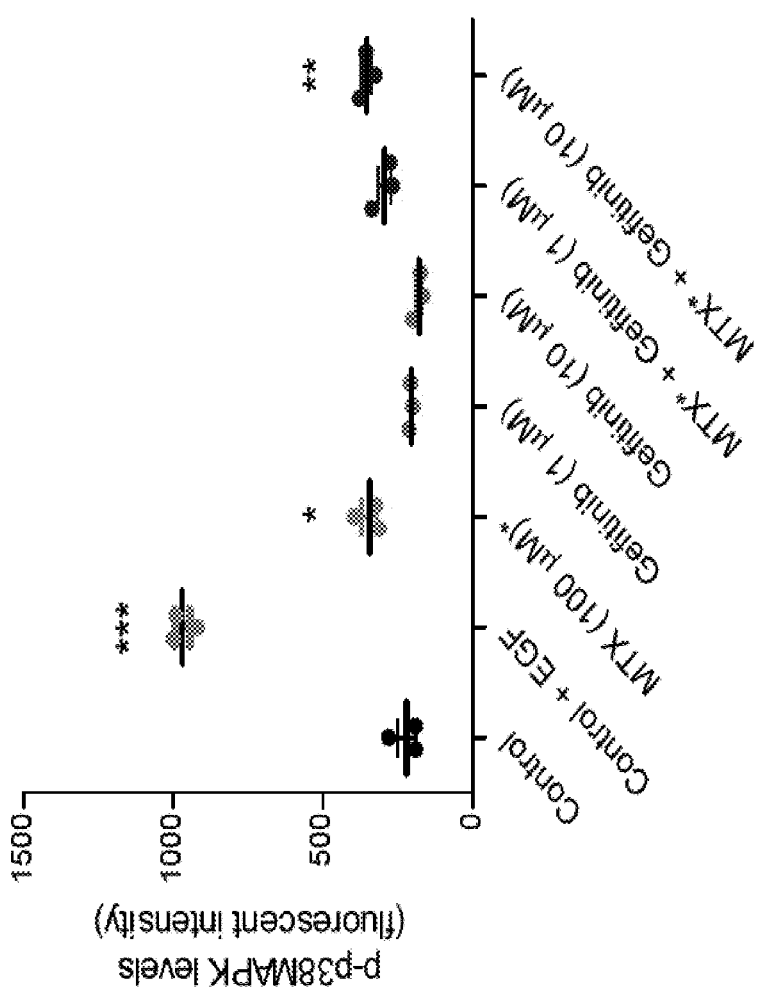
Figure 12C:
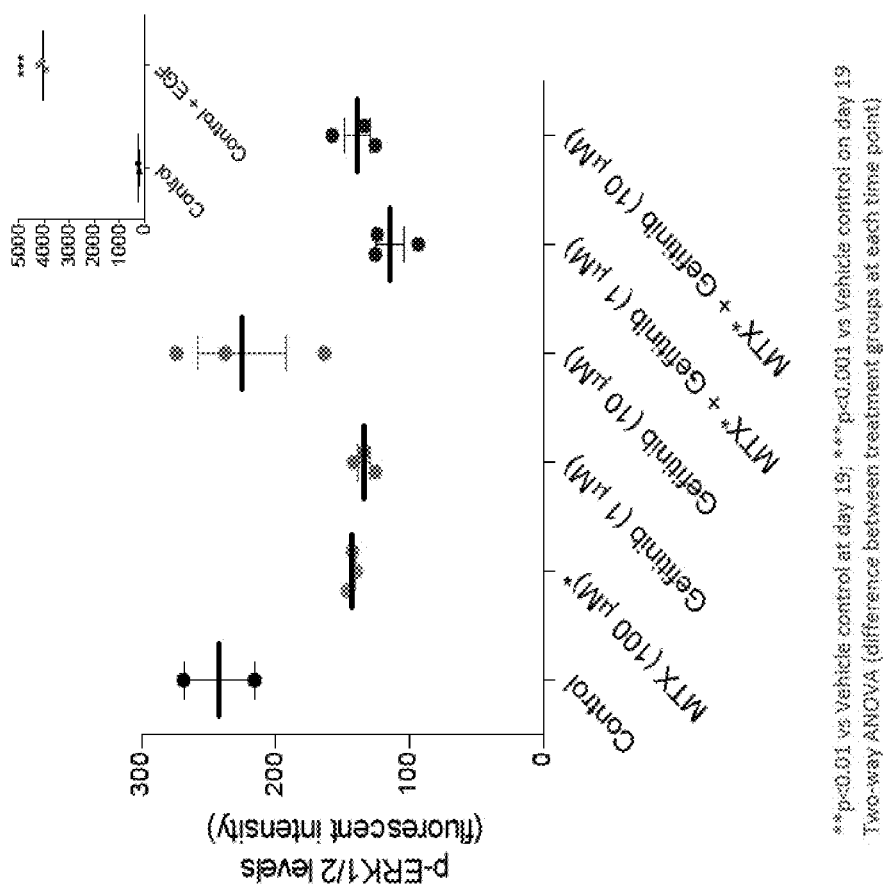
Figure 12D:
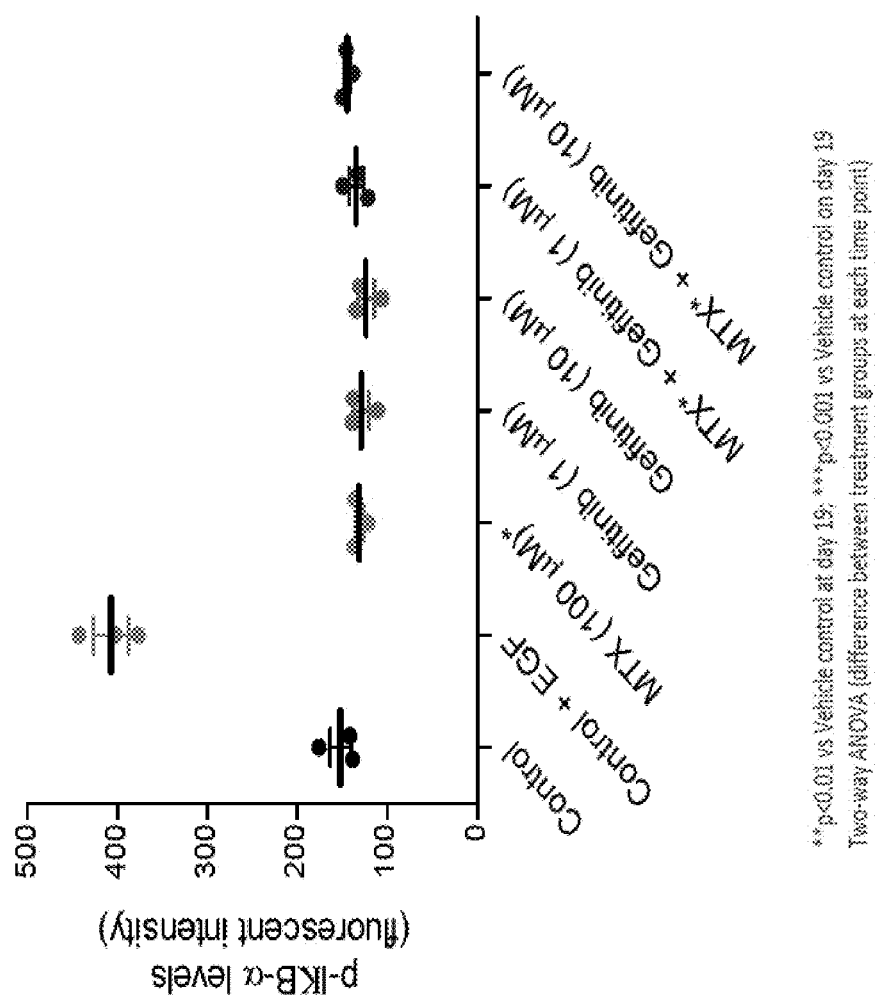

EGF induced significant phosphorylation of all molecules, which was potently blocked by gefitinib (FIGS. 12A, 12B, 12C and 12D). MTX treatment was associated with a significant increase in Akt phosphorylation (FIG. 12A), which was blunted by gefitinib in a dose dependent manner. For p38-MAPK, ERK and IKB-α, the different treatments suppressed EGF induced phosphorylation, but there were no obvious trends (FIGS. 12B, 12C and 12D). The inventors speculate one reason why combination treatment may have supra-additive potency in cell killing is that a compensatory survival response of Akt phosphorylation induced by MTX is blocked by gefitinib.

Figure 13B:
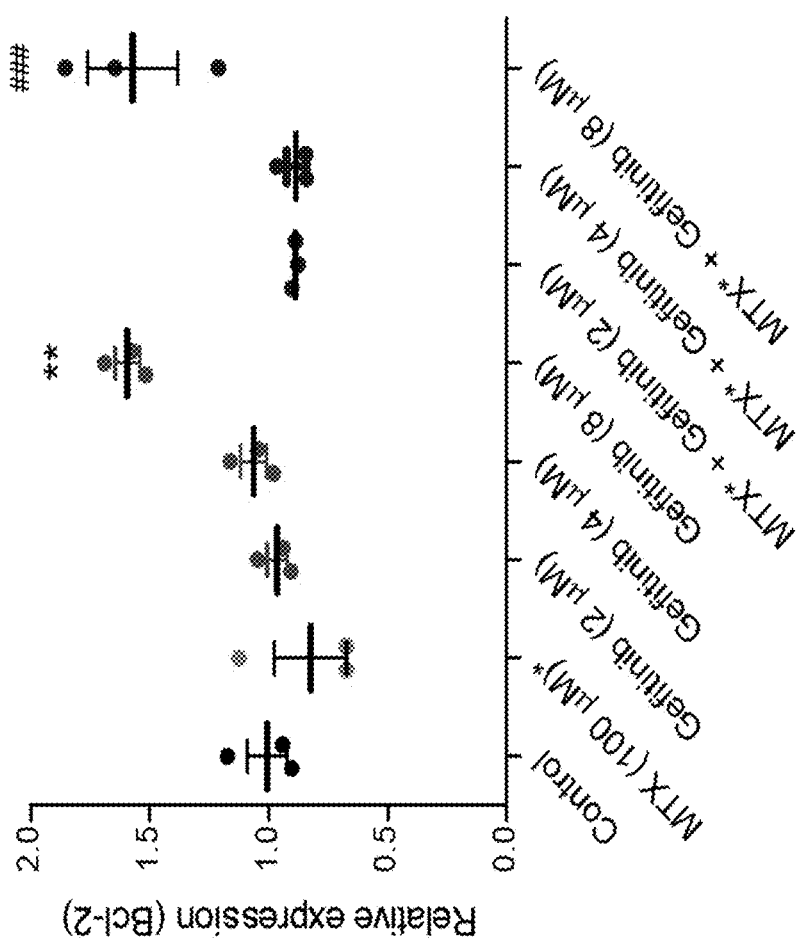
FIG. 13 mRNA expression of (A) Bim and (B) Bcl-2 and (C) M30 staining measured by FACS analysis after treatment of JEG3 cells with MTX±gefitinib for 48 (Bim and Bcl-2) or 72 hours (M30 antibody). Results of A-C are representative of at least two independent experiments. Mean of triplicates±S.E.M. shown for all results. Comparisons were done using one-way ANOVA with Bonferroni post hoc test: ≠P<0.05 vs gefitinib at 8 µM concentration, P<0.01 vs control, *P<0.001 vs control, ##P<0.01 vs MTX, ###P<0.001 vs MTX.

The inventors then investigated apoptosis after 48 hours of drug treatment in JEG3 cells. They first measured RNA expression of five major pro and anti-apoptotic genes. Bim (Pro-apoptotic Bcl-2 family member, FIG. 13A) and Bcl-2 (anti-apoptotic, FIG. 13B) expression increased at the highest concentrations of combination gefitinib and MTX, and there were no obvious trends in the expression of Survivin, Bcl-2 and Bcl-xL (data not shown). One possible explanation for these ambiguous findings is that most cells were either killed, or too compromised to mount robust transcriptional responses to stimuli by 48 hours post treatment.

Figure 13C:
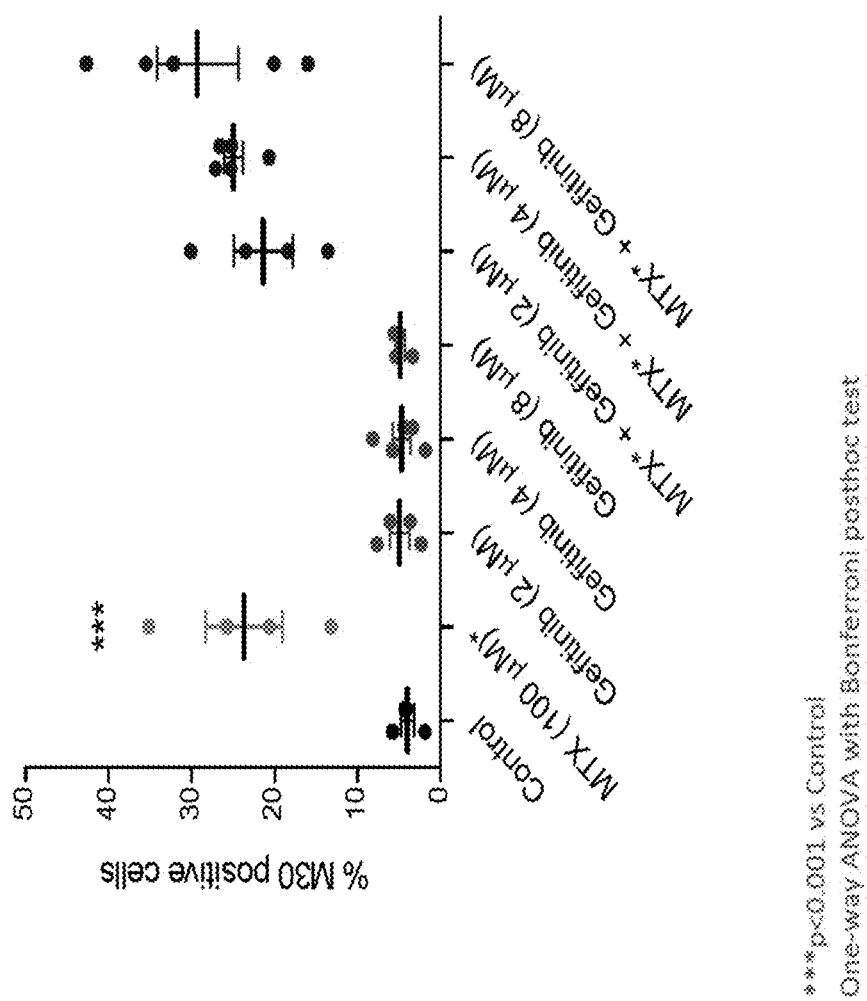

Therefore, the inventors performed FACS sorting using the M30 antibody that detects caspase-cleaved cytokeratin 18, a marker of early apoptosis which persists in cells (Ueno T et al., (2005) Biomed Pharmacother 59 Suppl 2, S359-362). There was increased expression in MTX alone compared to single agent gefitinib, and a non-significant trend towards increasing expression when increasing doses of gefitinib were added to MTX (FIG. 13C). The inventors conclude that combination treatment may increase apoptosis in placental cells.

The inventors have found that the addition of an EGFR inhibitor, gefitinib to MTX is supra-additive in killing placental cells. The clinical implication is that the addition of oral gefitinib to the current protocol of MTX injection(s) may be effective in resolving unruptured ectopics of larger size compared to existing medication based protocols that use MTX alone. Given MTX is available in tablet form, the possibility exists of a tablet only regimen to replace surgical intervention.

Unlike malignancies where escape mechanisms makes cure difficult (Ciardiello F & Tortora G (2008) *N Engl J Med* 358:1160-1174), inducing a major disruption to an ectopic pregnancy may be enough to effect cure since the maternal immune system should be able to clear the regressing ectopic. EGFR inhibitors are generally well tolerated with a very mild toxicity profile, even with chronic administration (van Zandwijk N (2003) *Br J Cancer* 89 Suppl 2 S9-14). The risk of side effects could be further minimised with short term dosing.

A medication-based alternative to surgery may have many advantages. It could be cheaper, safer and avoids further injury or removal of the fallopian tube, which may be fertility preserving. It could be particularly useful for ectopic pregnancies in lodged in caesarean section scars, the cervix and the uterine cornua. These are particularly dangerous and are notoriously difficult to manage without resorting to hysterectomy (Chetty M & Elson J (2009) *Best Pract Res Clin Obstet Gynaecol* 23, 529-538).

A medication-based treatment may have significant impact on maternal mortality in the developing world where deaths from ectopic pregnancies are likely to be high. The lack of access to expensive and skilled surgical care is probably an important contributor to maternal losses. Being potentially cheaper and much less complicated to administer, a medical treatment could be accessed by more women in the developing world, potentially saving many lives.

The invention claimed is:

1. A method of treating ectopic pregnancy in a subject comprising administering to the subject a composition comprising gefitinib and methotrexate.

2. The method according to claim 1, wherein the gefitinib is administered in combination with the methotrexate.

3. The method according to claim 1, wherein the gefitinib and the methotrexate are administered concurrently or sequentially.

4. The method according to claim 1, wherein the gefitinib and the methotrexate are administered orally to the subject.

5. The method according to claim 1, comprising the additional step of first diagnosing an ectopic pregnancy in a subject.

6. The method according to claim 5, comprising the additional step of measuring the concentration of β-human chorionic gonadotropin (β-hCG) in the subject's serum, blood or urine wherein a reduction in the concentration of p-hCG is predictive of successful treatment of the ectopic pregnancy.

7. The method according to claim 6, wherein the reduction of β-hCG concentration is at least 15% between day 4 and day 7, and wherein day 1 is the first date of administering methotrexate.

8. The method according to claim 6, wherein the β-hCG concentration is reduced to pre-pregnancy levels (<5 IU/L) following administration of the composition.

9. A method of treating an ectopic pregnancy having one or more of the following characteristics selected from the group consisting of:
   (i) a gestational sac size in the range of from about 0.5 cm to about 10 cm; and
   (ii) a β-hCG concentration in the range of from about 200 to about 100,000 IU/L;
   wherein the method comprises administering to the subject a composition comprising gefitinib and methotrexate.

10. The method according to claim 9, wherein the gestational sac size is in the range of from about 1 cm to about 8 cm.

11. The method according to claim 9, wherein the gestational sac size is in the range of from about 3 cm to about 6 cm.

12. A method according to claim 9, wherein the gestational sac size is in the range of from about 3 cm to about 5 cm.

13. A method for predicting whether a subject's ectopic pregnancy will be successfully treated comprising:
   (i) administering to the subject one or more doses of gefitinib and methotrexate; and
   (ii) measuring the concentration of β-hCG in the subject's serum, blood or urine;
   wherein a reduction in the concentration of β-hCG by at least 15% between day 4 and day 7 is predictive of successful treatment of the ectopic pregnancy and wherein day 1 is the first day of methotrexate dose.

14. The method according to claim 13, wherein the gefitinib and methotrexate are administered concurrently or sequentially.

* * * * *